(12) United States Patent
Seykora et al.

(10) Patent No.: US 11,504,173 B2
(45) Date of Patent: Nov. 22, 2022

(54) BONE-STABILIZING DEVICE HAVING A PIVOTABLE BUTTRESS MEMBER

(71) Applicant: Acumed LLC, Hillsboro, OR (US)

(72) Inventors: Andrew W. Seykora, Portland, OR (US); Mark B. Sommers, Beaverton, OR (US); Caleb Abraham Martin, Beaverton, OR (US); Stephen Young, Portland, OR (US); Brian R. Conley, Portland, OR (US); Larry W. Ehmke, Portland, OR (US)

(73) Assignee: Acumed LLC, Hillsboro, OR (US)

( * ) Notice: Subject to any disclaimer, the term of this patent is extended or adjusted under 35 U.S.C. 154(b) by 0 days.

(21) Appl. No.: 17/022,716

(22) Filed: Sep. 16, 2020

(65) Prior Publication Data

US 2022/0079636 A1    Mar. 17, 2022

(51) Int. Cl.
*A61B 17/80*      (2006.01)

(52) U.S. Cl.
CPC ...... *A61B 17/8004* (2013.01); *A61B 17/8023* (2013.01); *A61B 17/8061* (2013.01)

(58) Field of Classification Search
CPC . A61B 17/80; A61B 17/8004; A61B 17/8023; A61B 17/8061
See application file for complete search history.

(56) References Cited

U.S. PATENT DOCUMENTS

| | | | | |
|---|---|---|---|---|
| 5,681,313 A * | 10/1997 | Diez | ............... | A61B 17/8004 606/282 |
| 6,852,113 B2 * | 2/2005 | Nathanson | ......... | A61B 17/8009 606/71 |
| 7,090,676 B2 * | 8/2006 | Huebner | ............ | A61B 17/8061 606/71 |
| 8,328,848 B2 * | 12/2012 | Lowery | ............. | A61B 17/7055 606/248 |
| 9,011,503 B2 | 4/2015 | Duggal et al. | | |

(Continued)

FOREIGN PATENT DOCUMENTS

| CN | 2320211 Y | 5/1999 |
|---|---|---|
| CN | 200973745 Y | 11/2007 |

(Continued)

OTHER PUBLICATIONS

M.E. Muller et al., "3.5mm LCP Clavicle Hook Plates. Part of the Synthes locking compression plate (LCP) system." Manual of Internal Fixation, 1991, 3rd Edition, Berlin: Springer-Verlag, 24 pages.

(Continued)

*Primary Examiner* — Larry E Waggle, Jr.
(74) *Attorney, Agent, or Firm* — K&L Gates LLP

(57) ABSTRACT

Devices and methods for stabilizing bone. An exemplary device may comprise a plate, an arm, and a buttress member. The plate may define one or more apertures configured to receive one or more fasteners that secure the plate onto a first bone region. The arm may project from an edge of the plate. The buttress member may be connected pivotably to an end of the arm. The buttress member may be configured to be pivoted by contact with a second bone region to conform an orientation of the buttress member to the second bone region, and may apply compression to, and/or support, the second bone region.

21 Claims, 20 Drawing Sheets

(56) References Cited

U.S. PATENT DOCUMENTS

| | | | |
|---|---|---|---|
| 9,072,557 B2 | 7/2015 | Fierlbeck et al. | |
| 9,259,322 B2 * | 2/2016 | Embleton | A61B 17/8023 |
| 9,622,867 B2 | 4/2017 | Embleton et al. | |
| 10,182,856 B2 * | 1/2019 | Reuter | A61B 17/1728 |
| 10,588,679 B2 | 3/2020 | Kukla et al. | |
| 2003/0114856 A1 | 6/2003 | Nathanson et al. | |
| 2005/0240187 A1 | 10/2005 | Huebner et al. | |
| 2009/0012569 A1 | 1/2009 | Dall et al. | |
| 2013/0006307 A1 | 1/2013 | Robinson et al. | |
| 2015/0173812 A1 | 6/2015 | Masson | |
| 2015/0216574 A1 | 8/2015 | Huebner et al. | |

FOREIGN PATENT DOCUMENTS

| | | | |
|---|---|---|---|
| CN | 201987653 U | 9/2011 | |
| CN | 103610493 A | 3/2014 | |
| CN | 203576625 U | 5/2014 | |
| CN | 104116553 A | 10/2014 | |
| CN | 203970524 U | 12/2014 | |
| CN | 204318886 U | 5/2015 | |
| CN | 104758041 A | 7/2015 | |
| CN | 204600646 U | 9/2015 | |
| CN | 204600647 U | 9/2015 | |
| CN | 205144701 U | 4/2016 | |
| CN | 205569052 U | 9/2016 | |
| CN | 106137367 A | 11/2016 | |
| CN | 206183359 U | 5/2017 | |
| GB | 2546089 A | 7/2017 | |
| KR | 101679323 B1 | 12/2015 | |
| WO | 8201645 A1 | 5/1982 | |
| WO | 2016074505 A1 | 5/2020 | |

OTHER PUBLICATIONS

Qingjun Liu et al., "Surgical Treatment for Unstable Distal Clavicle Fracture with Micromovable and Anatomical Acromioclavicular Plate" Int J Med Sci 2012; 9(4): 301-305. doi:10.7150/ijms.4425. Available from http://www.medsci.org/v09p0301.htm, 7 pages.

International Search Report corresponding to related International Patent Application No. PCT/US2021/050441 dated Dec. 30, 2021, 3 pages.

International Written Opinion corresponding to related International Patent Application No. PCT/US2021/050441 dated Dec. 30, 2021, 8 pages.

* cited by examiner

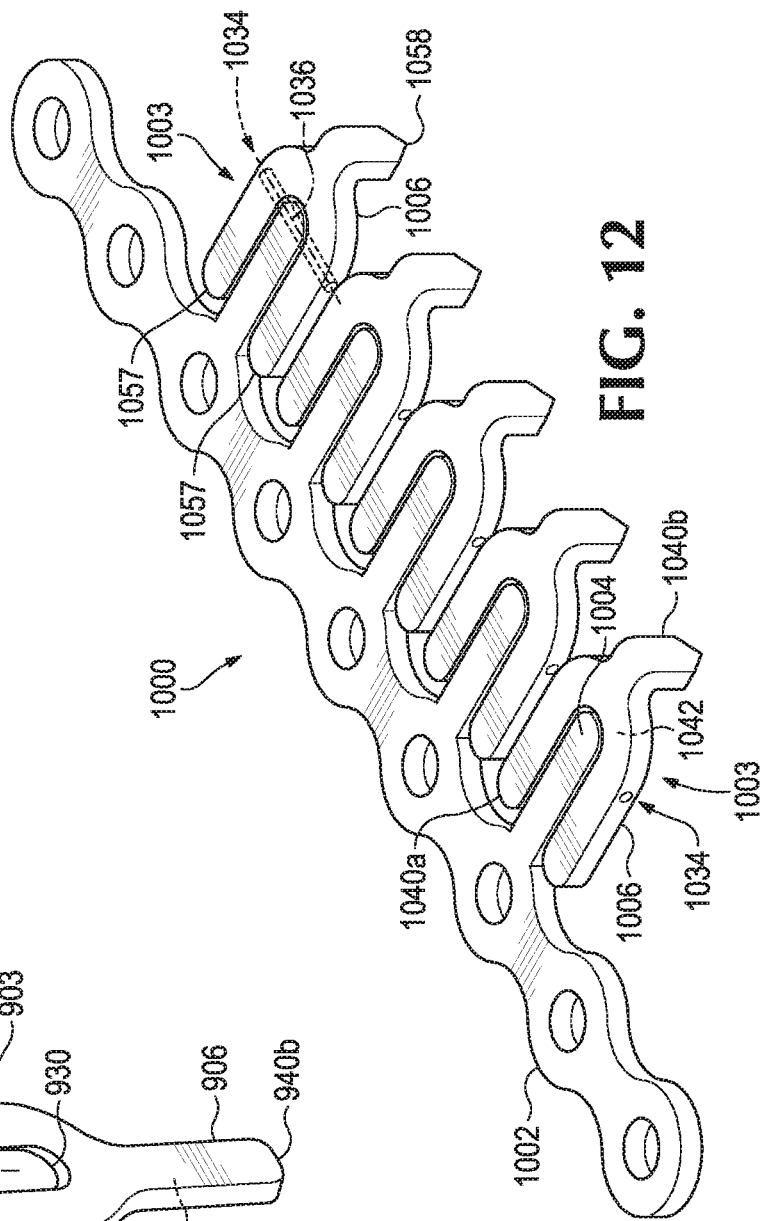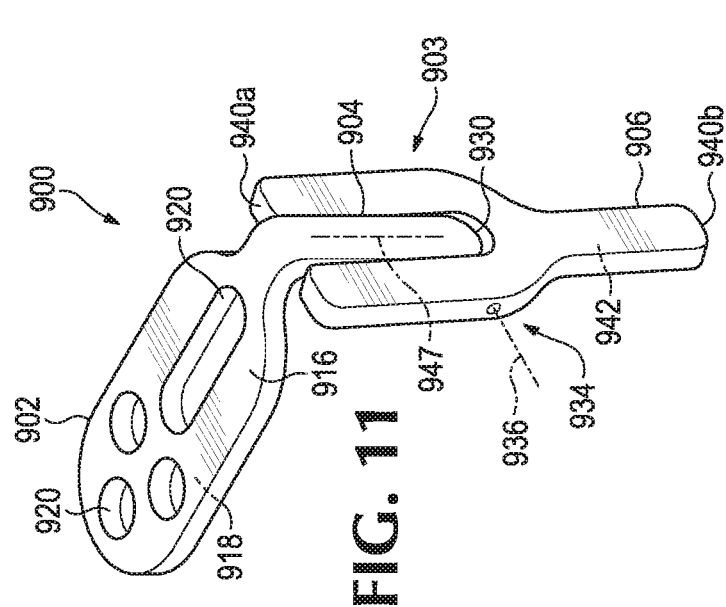

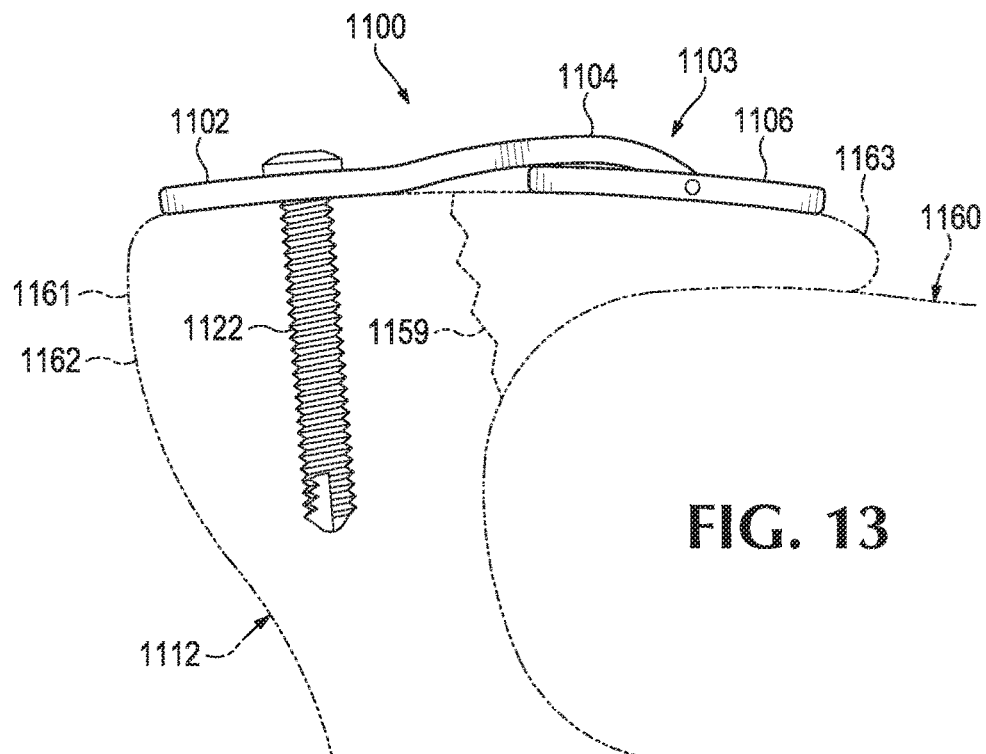
FIG. 13
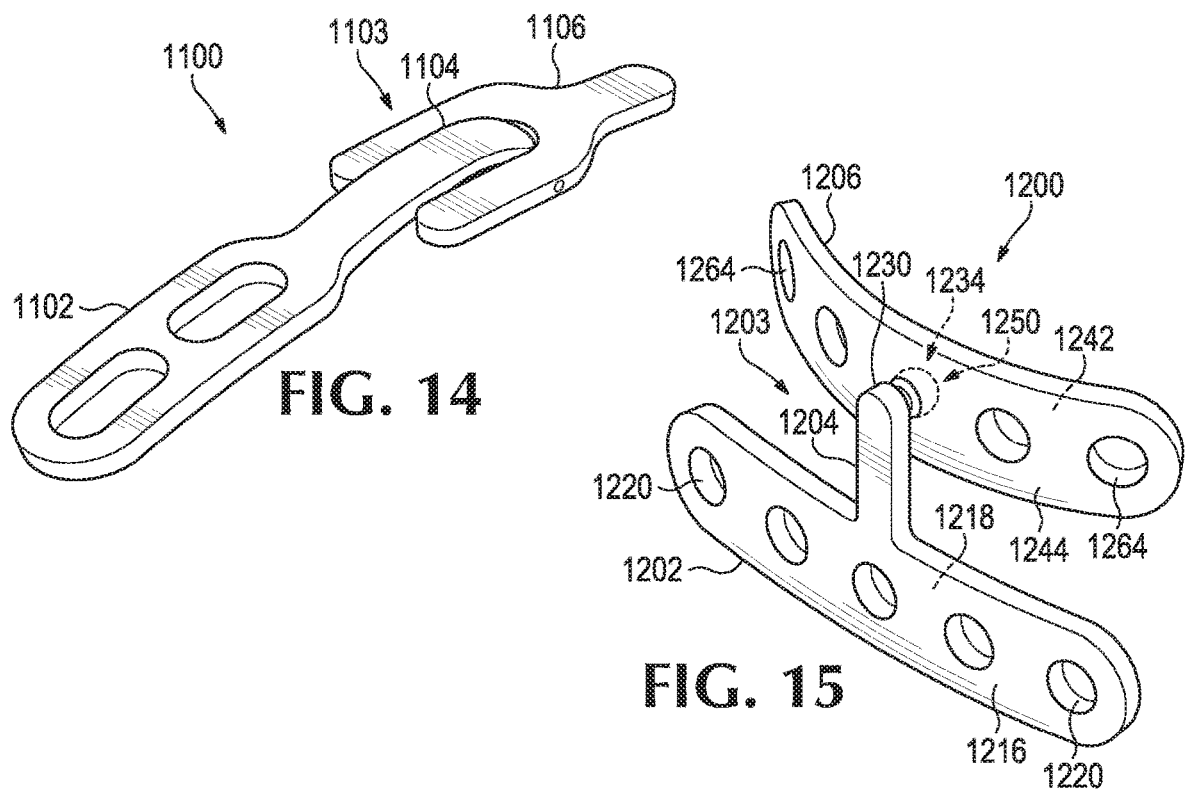
FIG. 14
FIG. 15

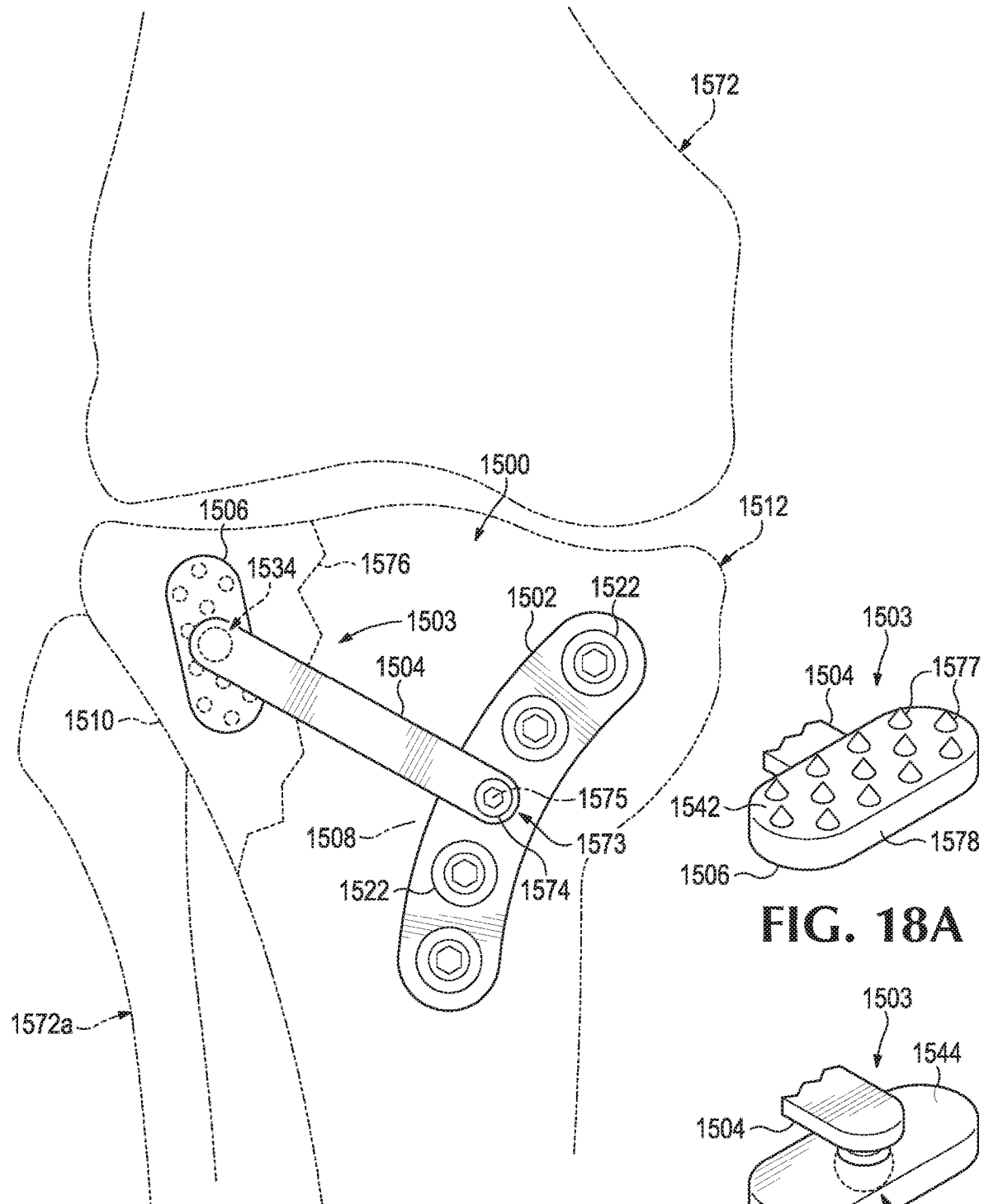
FIG. 18
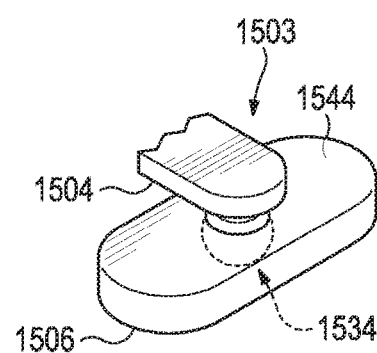
FIG. 18A
FIG. 18B

BONE-STABILIZING DEVICE HAVING A PIVOTABLE BUTTRESS MEMBER

BACKGROUND

Various types of plate-based devices for stabilizing bone are known. In some cases, the plate-based device relies on fasteners, such as bone screws, to directly secure the plate-based device to each bone or bone fragment to be stabilized. With this design, installation of the fasteners may be unduly labor intensive and time-consuming, and unnecessarily invasive. In other cases, the plate-based device contacts, but is not secured to, one of the bones or bone fragments being stabilized. This design simplifies installation of the plate-based device but may cause other problems, such as a poor fit and/or erosion of bone, among others. An improved plate-based device is needed for stabilizing bone.

SUMMARY

The present disclosure provides devices and methods for stabilizing bone. An exemplary device may comprise a plate, an arm, and a buttress member. The plate may define one or more apertures configured to receive one or more fasteners that secure the plate onto a first bone region. The arm may project from an edge of the plate. The buttress member may be connected pivotably to an end of the arm. The buttress member may be configured to be pivoted by contact with a second bone region to conform the orientation of the buttress member to the second bone region, and may apply compression to, and/or support, the second bone region.

BRIEF DESCRIPTION OF THE DRAWINGS

FIG. 11 is an isometric view of an implantable device configured to be secured to the pelvis and including a plate, an arm, and a buttress member.

FIG. 12 is an isometric view of another implantable device configured to be secured to the pelvis near an acetabulum thereof, and including a plate, a series of arms, and a respective buttress member connected to each of the arms.

FIG. 13 is a side elevation view of an implantable device secured to a fractured olecranon, where the device includes a plate, an arm, and a buttress member.

FIG. 14 is an isometric view of the implantable device of FIG. 13 taken in the absence of bone.

FIG. 15 is an isometric view of still another implantable device configured to be secured to the pelvis, where the device includes a plate, an arm, and a buttress member.

FIG. 18 is a top plan view of an implantable device secured to a fractured proximal tibia, where the device includes a plate, an arm, and a buttress member, where the plate and the arm are formed separately from one another, and where the arm has an adjustable, lockable orientation with respect to the plate.

FIG. 18A is a fragmentary view of the device of FIG. 18 taken around the buttress member, with a bone-engaging surface of the buttress member facing up and including a plurality of spikes.

FIG. 18B is another fragmentary view of the device of FIG. 18 taken around the buttress member and representing approximately the same fragmentary portion of the device as in FIG. 18A except with the device inverted.

DETAILED DESCRIPTION

Figure 1:
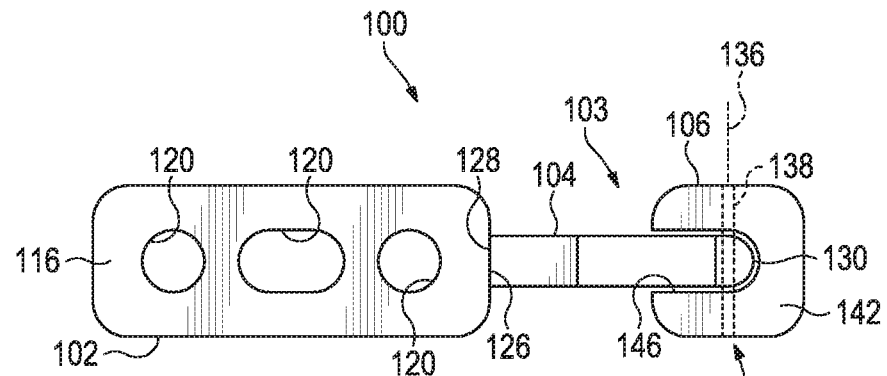
FIG. 1 is a top plan view of an implantable device to stabilize bone, where the implantable device includes a plate and an outrigger, where the outrigger includes an arm projecting from an edge of the plate and a buttress member pivotably connected to an end of the arm, and where the buttress member has a bone-engaging surface that is orientable by contact with bone, to an orientation that is at least generally parallel to a top surface of the plate.

The present disclosure provides devices and methods for stabilizing bone. An exemplary device may comprise a plate, an arm, and a buttress member. The plate may define one or more apertures configured to receive one or more fasteners that secure the plate onto a first bone region. The arm may project from an edge of the plate. The buttress member may be connected pivotably to an end of the arm. The buttress member may be configured to be pivoted by contact with a second bone region to conform the orientation of the buttress member to the second bone region, and may apply compression to, and/or support, the second bone region.

The bone-stabilizing device may have various advantages, including any of the following. The device may be easier to install by using fewer fasteners. The device may be self-orienting with respect to bone, which may provide a dynamic fit to bone. Bone may be damaged less (e.g., bone erosion may be minimized). Compression (pressure) and/or support may be provided to a bone region without the need to secure the device to the bone region with fasteners.

Further aspects of the present disclosure are described in the following sections: (I) overview of bone-stabilizing devices, and (II) examples.

I. OVERVIEW OF BONE-STABILIZING DEVICES

This section provides an overview of the bone-stabilizing, implantable devices of the present disclosure, as exemplified by a device 100 including a plate 102 (interchangeably called a mounting plate) and an outrigger 103 that projects from plate 102. Outrigger 103 may, for example, provide a hook and includes an arm 104 and a buttress member 106; see FIGS. 1-3. Any suitable combination of the elements and features described in this section may be incorporated into any of the devices of the present disclosure.

Figure 2:
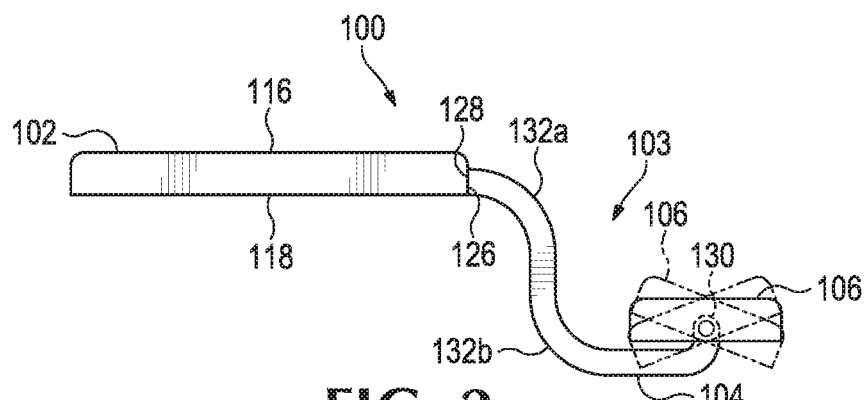
FIG. 2 is a side view, taken at elevation, of the implantable device of FIG. 1, with pivotal reorientation of the buttress member indicated using broken lines.
Figure 3:
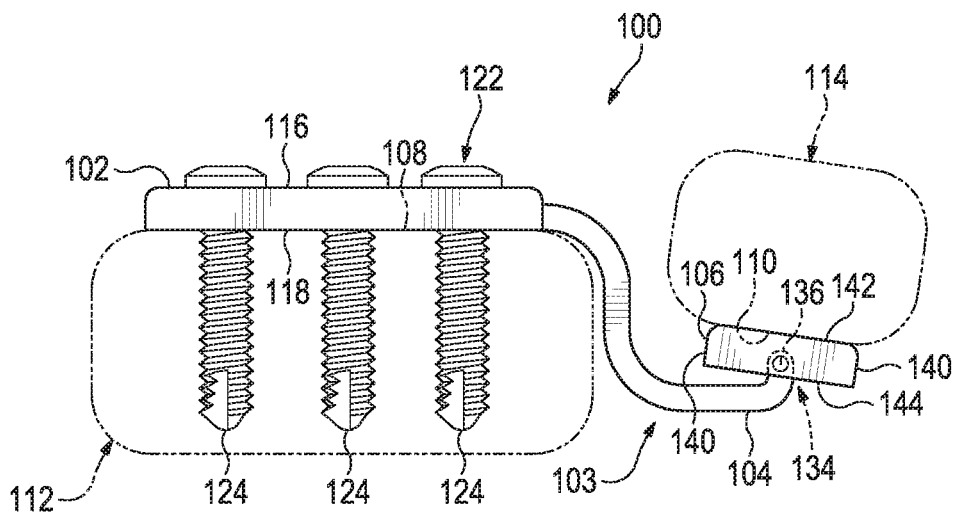
FIG. 3 is another side view of the implantable device of FIG. 1, taken generally as in FIG. 2, with the plate secured to a first bone region using a plurality of fasteners, and with the buttress member pressing against a second bone region while the orientation of the buttress member conforms to a local surface contour of the second bone region.

Device 100 is shown in isolation in FIGS. 1 and 2 and in an implanted configuration engaged with first and second bone regions 108, 110 in FIG. 3. Bone regions 108, 110 may be provided by respective bones 112, 114 or the same bone. Each device of the present disclosure can stabilize bone by restricting movement of first and second bone regions relative to one another. For example, the device can prevent the bone regions from moving closer to one another (i.e., setting a minimum separation between the bone regions along an axis extending through the bone regions) (e.g., see Examples 1 and 4), from moving away from one another (i.e., setting a maximum separation between the bone regions along the axis) (e.g., see Examples 2 and 3), and/or from shifting transversely relative to one another in a particular direction orthogonal to the axis (e.g., see FIG. 3). Accordingly, the devices of the present disclosure have many uses, such as stabilizing fractured or cut bones and/or joints or other connections between bones, to facilitate healing of bone and/or soft tissue, enable proper function, and/or avoid injury.

Plate 102 has an outer surface 116 opposite an inner surface 118. Outer surface 116 can be called a top surface, and inner surface 118 can be called a bottom surface, irrespective of the orientation of device 100 after implantation. When plate 102 is placed onto first bone region 108, outer surface 116 faces away from first bone region 108, and inner surface 118 faces toward, and optionally contacts, first bone region 108 (see FIG. 3).

One or more apertures 120 may be defined by plate 102. Each aperture 120 may extend through plate 102 between outer surface 116 and inner surface 118. The aperture may have any suitable shape, such as circular, or elongated parallel to surfaces 116, 118 (to form a slot), or the like. Plate 102 may have at least one aperture 120 that is circular, at least one aperture 120 that is a slot, or both, among others. Each aperture 120 may have any suitable size based on its intended use. For example, each aperture 120 may be configured to receive a fastener 122, such as a bone screw 124, that attaches plate 102 to first bone region 108 (see FIG. 3). In other embodiments, one or more apertures of the plate may be sized and/or shaped to receive another type of fastener, such as a pin, wire, suture, or the like.

Arm 104 of outrigger 103 projects from an edge 126 of plate 102 and extends to buttress member 106. For example, arm 104 may project from an end of plate 102, such as longitudinally (e.g., axially from the plate), as shown in FIG. 1, or, in other examples, may project laterally from a lateral edge of the plate (e.g., see Examples 3, 6, 9, 11, and 16), among others. The arm may be formed integrally with, or separately from, plate 102. If formed separately from the plate, the arm may be adjustably positionable and/or orientable with respect to the plate. For example, the arm may be slidable to adjust a length of the arm that projects from the edge of the plate (e.g., see Examples 7 and 17-19), and/or may be pivotable with respect to the plate to adjust an orientation of the arm relative to the plate (e.g., see Example 14). From any of these movable configurations, the arm may be fixedly attachable (i.e., lockable) to the plate at a selected position and/or orientation after adjusting the arm's position/orientation. In other examples, the arm may be dynamically slidable and/or pivotable after implantation during use in the subject.

Arm 104 may be elongated between a proximal end 128 and a distal end 130. Proximal end 128 may be located adjacent, and/or may be continuous with, plate 102. Distal end 130 may be located adjacent, and connected to, buttress member 106. Arm 104 may extend along a nonlinear path, which may be smoothly curved or may have one or more distinct bends (i.e., bent sections) 132a, 132b (see FIG. 2). In other embodiments, the arm may follow a linear path between the arm's proximal and distal ends (e.g., see Examples 1 and 5-7). More generally, the shape of the arm may determine where the buttress member is positioned with respect to the plate, and, at least to some extent, how the buttress member is oriented generally (e.g., compare FIG. 3 with Examples 1, 2, and 8). The shape of the arm may primarily determine a vertical offset, if any, of the plate and the buttress member from one another. For example, in FIG. 3, buttress member 106 is located below inner surface 118 of plate 102. The shape of the arm also may determine an axial offset (e.g., see FIG. 3) and/or a lateral offset (e.g., see Examples 6 and 11) of the plate and the buttress member from one another.

Device 100 has only one outrigger 103. However, in other embodiments, the device may have two or more outriggers each including an arm and a buttress member (e.g., see Examples 3, 4, 6, and 9). The two or more arms of the outriggers may project from the same lateral edge or the same end of the plate, from opposite lateral edges of the plate, from opposite ends of the plate, from a lateral edge and an end of the plate, or a combination thereof, among others.

A buttress member, as used herein, is any structure capable of applying compression to, and/or supporting, a bone region at a surface thereof. Due to the pivotability of the buttress member, the compression may be applied in a more distributed, balanced manner to avoid point loading and erosion of bone. The compression may be described as pressure on the bone region.

Buttress member 106 of outrigger 103 has a pivotable connection 134 to distal end 130 of arm 104 (see FIG. 1). The pivotable connection permits buttress member 106 to pivot with respect to arm 104 about only a single pivot axis 136, which may, for example, be defined by a pin 138. In some embodiments, single pivot axis 136 may be substantially (within 10 degrees) or generally (within 20 degrees) parallel to plate 102, and/or may be substantially (within 10 degrees) or generally (within 20 degrees) orthogonal to a line parallel to a longitudinal axis of plate 102. In other embodiments, the single pivot axis may be transverse to the plate (e.g., see Example 1), such as substantially or generally orthogonal to the plate (as defined above). In other examples, the pivotable connection between the arm and the buttress member permits more than one degree of rotational freedom such that the buttress member is pivotable with respect to the arm about two or more non-parallel axes (and in each of two or more non-parallel planes) (e.g. see Examples 5, 11, 14, and 20).

Pivotable connection 134 and/or pivot axis 136 may be located centrally intermediate opposite edge regions 140 of the buttress member 106 (see FIG. 3). This central location facilitates distributing and balancing the forces applied to second bone region 110 by buttress member 106. Similarly, if the pivotable connection between the arm and the buttress member permits pivotal motion in each of two or more non-parallel planes, the pivotable connection may define a pivot point located at a centroid of buttress member 106, where the centroid is the center of mass of the buttress member.

Buttress member 106 has an inner surface 142 (also called a bone-engaging surface) through which the buttress member applies compression to second bone region 110 (see FIG. 3). Contact between inner surface 142 and second bone region 110 can cause buttress member 106 to pivot, which conforms the orientation of inner surface 142 more closely to that of a local surface contour of second bone region 110. Accordingly, the buttress member may be described as a leveling member that adjusts its orientation to match that of second bone region 110 when the leveling member is placed against the second bone region.

Arm 104 may approach pivotable connection 134 from an outer surface 144 of buttress member 106 (see FIG. 3). The arm may extend into a slot 146 defined by buttress member 106 (see FIG. 1). Slot 146 may be configured to reduce obstruction of pivotal motion of buttress member 106 by arm 104, to permit a greater angular range of pivotal motion of buttress member 106, such as an angular range of at least 10, 20, or 30 degrees, among others.

Inner surface 142 may have any suitable neutral orientation with respect to plate 102 and a longitudinal axis thereof. The neutral orientation is defined at the midpoint within the range of pivotal motion of the buttress member. As indicated in FIG. 2, the neutral orientation of inner surface 142 is substantially or generally parallel to plate 102, such that inner surface 142 faces in the substantially or generally opposite direction to inner surface 118 of plate 102. In other embodiments, inner surface 142 of the buttress member may face in substantially or generally the same direction as inner surface 118 of plate 102. In yet other embodiments, the neutral orientation of the inner surface of the buttress member may be transverse (such as substantially or generally orthogonal) to the plate (e.g., see Examples 1, 2, 16, 17, and 19). In these embodiments, the inner surface of the buttress member may face generally towards the plate (see Examples 2, 16, and 17) or generally away from the plate (see Examples 1 and 19), and/or generally towards the inner surface of another buttress member of the device (see Example 3).

Buttress member 106 may be configured to engage, and apply compression to and/or support, second bone region 110 without the need to be secured to the second bone region using a separate fastener(s). Accordingly, as shown, buttress member 106 may not define any aperture(s) configured to receive a separate fastener(s) for securing the buttress member to second bone region 110. In some embodiments, buttress member 106 may fail to define any circumferentially-bounded aperture(s) that extend through the buttress member between inner surface 142 and outer surface 144. In other embodiments, the buttress member may define one or more apertures that extend through the buttress member between inner and outer surfaces thereof (e.g., see Examples 11, 15, and 18). However, even if such apertures are present, they are not necessarily occupied by fasteners, and, even if occupied by one or more separate fasteners, such as bone screws, pins, wires, or sutures, the fasteners are not required for the buttress member to apply compression to the second bone region. Instead, the force for applying this compression may be transmitted to the buttress member from the plate via the arm and/or is applied as a counter-compression in response to compression applied to the buttress member by the second bone region.

Buttress member 106 is shown as having a substantially featureless inner surface 142. However, in other embodiments, the inner surface of the buttress member may form one or more spikes or other protrusions (e.g., see Examples 14, 16, and 20). The spikes or other protrusions may function to resist slippage of the buttress member when engaged with the second bone region.

The buttress member of the bone-stabilizing devices of the present disclosure may be configured to be freely pivotable before implantation. More specifically, the buttress member may be freely pivotable with respect to the arm over a continuous range of orientations while remaining connected to the arm. Alternatively, the buttress member may be adjustable between a restrained configuration and a released configuration during or after implantation. For example, the bone-stabilizing device may have at least one friction feature or detent that prevents the buttress member, in the restrained configuration, from pivoting relative to the arm until at least a threshold torque is applied to the buttress member. The buttress member is configured to be placed in the released configuration in response to application of at least the threshold torque, such that pivoting the buttress member after release requires application of less than the threshold torque. The threshold torque may be applied to the bone-stabilizing device before, during, or after implantation.

The bone-stabilizing devices of the present disclosure may be figured to stabilize any suitable bone(s) and/or regions thereof. Exemplary bones and bone regions that may be suitable include a proximal femur (see Example 15), a pelvis (see Examples 8, 9, and 11), a proximal tibia (see Example 14), a clavicle and acromion around an acromioclavicular joint (see Example 20), a glenoid or other articular region (see Example 13), a rib cage (see Example 12), an olecranon (see Example 10), or a proximal ulna and radius (see Example 16), among others.

The bone-stabilizing devices of the present disclosure may be formed of any suitable biocompatible and/or bioresorbable materials. Exemplary materials for a bone-stabilizing device include metal (e.g., titanium, stainless steel, cobalt chrome, etc.) or polymer for each of the device components, such as a plate, an arm, and a buttress member of the device. In some embodiments, the buttress member may have a radiolucent body (e.g., formed of polymer) and at least one radiopaque marker (e.g., formed of metal) attached to one another (e.g., see Example 20). The radiolucent body may provide an inner surface to contact bone, and at least a majority of the at least one radiopaque marker may be disposed inside the radiolucent body or may be disposed on the radiolucent body, among others.

II. EXAMPLES

The following examples describe further aspects of the bone-stabilizing devices and methods of the present disclosure. These examples are intended for illustration only and are not intended to limit the entire scope of the present disclosure.

Example 1. Device to Separate Bone Regions

Figure 4:
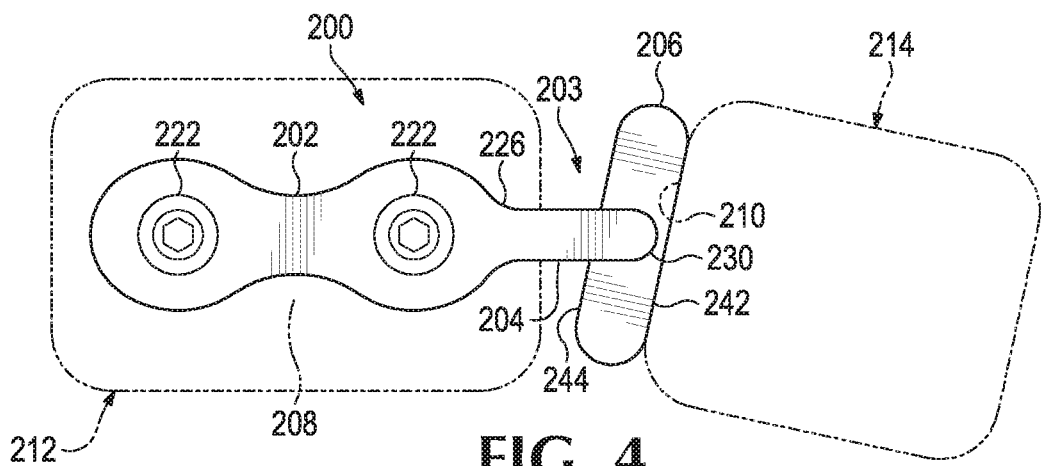
FIG. 4 is a top plan view of another implantable device to stabilize bone, where the implantable device is configured to keep regions of bone apart from one another, where the implantable device includes a plate, an arm, and a pivotable buttress member, where the buttress member is pivotable about an axis transverse to the plate and/or has a bone-engaging surface that is at least generally orthogonal to a top surface of the plate, and where the plate is secured to a first bone region using a plurality of fasteners, with the buttress member pressing against a second bone region while the orientation of the buttress member conforms to the local surface contour of the second bone region.
Figure 4A:
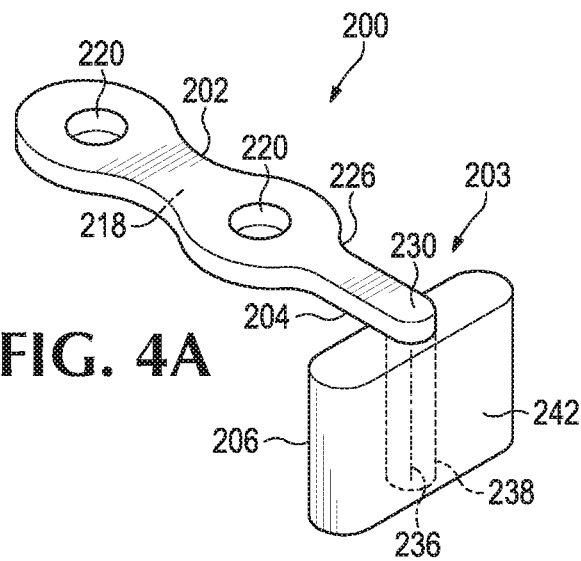
FIG. 4A is an isometric view of the implantable device of FIG. 4 taken in the absence of bone.

This example describes an exemplary bone-stabilizing device 200 to maintain a separation, such as a minimum separation, between a pair of bone regions 208, 210 provided by a pair of bones 212, 214 (or by a single bone); see FIGS. 4 and 4A.

Device 200 includes a plate 202 and an outrigger 203 projecting therefrom. Plate 202 defines apertures 220 to receive fasteners 222 that secure the plate onto first bone region 208.

Outrigger 203 has an arm 204 formed integrally with plate 202, and a buttress member 206 connected pivotably to a distal end 230 of arm 204. Arm 204 projects axially from plate 202, namely, from an edge 226 at one end of plate 202. In the depicted embodiment, arm 204 is linear but in other embodiments the arm may be nonlinear, as described elsewhere herein.

Buttress member 206 is pivotable about a single pivot axis 236 that is transverse to plate 202, such as substantially or generally orthogonal to plate 202 as shown (and as defined above). The term "transverse," as used in the present disclosure, means within 45 degrees of orthogonal. Pivot axis 236 is defined by a pin 238 projecting below an inner surface 218 of plate 202.

Buttress member 206 has a pair of surfaces 242, 244 arranged generally or substantially parallel to one another and pivot axis 236. Although surface 242 is contacting second bone region 210 in the depicted configuration, buttress member 206 may be pivoted approximately 180 degrees about pivot axis 236, such that surface 244 can be chosen to contact second bone region 210 upon implantation of device 200.

Example 2. Device to Limit Separation Between Bone Regions

Figure 5:
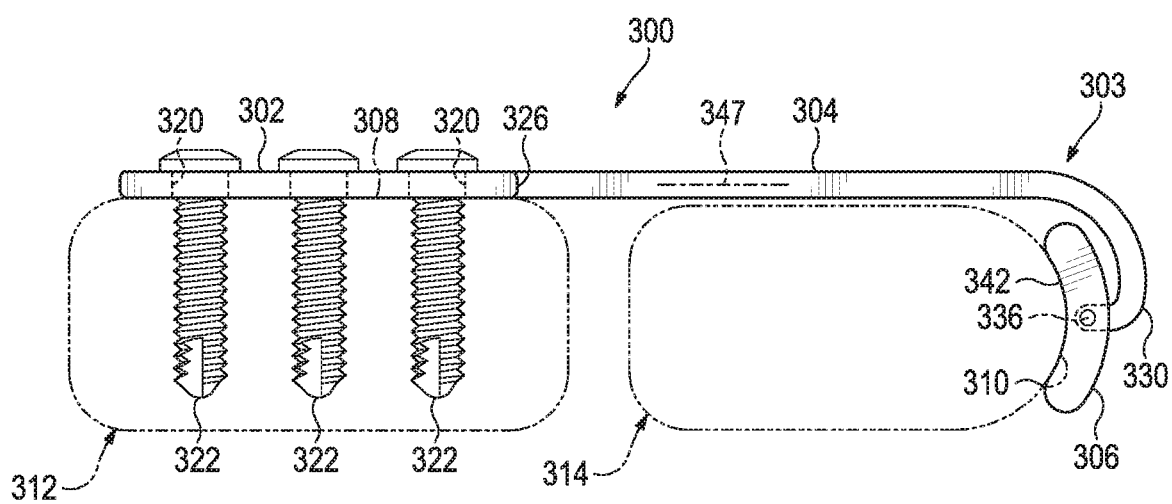
FIG. 5 is a side view, taken at elevation, of still another implantable device to stabilize bone, where the implantable device is configured to establish a maximum separation between bone regions, where the implantable device includes a plate, an arm, and a buttress member, where the buttress member is pivotable about an axis that is at least generally parallel to a top surface of the plate and/or has a bone-engaging surface that is orientable to face at least generally toward the plate, and where the plate is secured to a first bone region using a plurality of fasteners, with the buttress member pressing against a second bone region while the orientation of the buttress member conforms to a local surface contour of the second bone region.

This example describes an exemplary bone-stabilizing device 300 to limit the distance between a pair of bone regions 308, 310 provided by a pair of bones 312, 314 (or by a single bone); see FIG. 5.

Device 300 includes a plate 302 and an outrigger 303 projecting therefrom. Plate 302 defines apertures 320 to receive fasteners 322 that secure the plate to first bone region 308.

Outrigger 303 has an arm 304 formed integrally with plate 302, and a buttress member 306 connected pivotably to a distal end 330 of arm 304. Arm 304 is formed integrally with plate 302 and projects axially from plate 302, namely, from an edge 326 at one end of plate 302.

Buttress member 306 is pivotable about a single pivot axis 336 that is generally and/or substantially parallel to plate 302. Pivot axis 336 is transverse (e.g., generally or substantially orthogonal) to a long axis 347 defined by plate 302 and/or arm 304.

Buttress member 306 has a bone-engaging surface 342 to engage second bone region 310. Here, bone-engaging surface 342 is concave, but in other embodiments may be planar or convex, among others. Arm 304 may form a distal bend of at least about 90, 120, 150, or 180 degrees, such that bone-engaging surface 342 faces generally back toward plate 302, with buttress member 306 in a neutral orientation.

Example 3. Device Having a Pair of Embracing Outriggers

Figure 6:
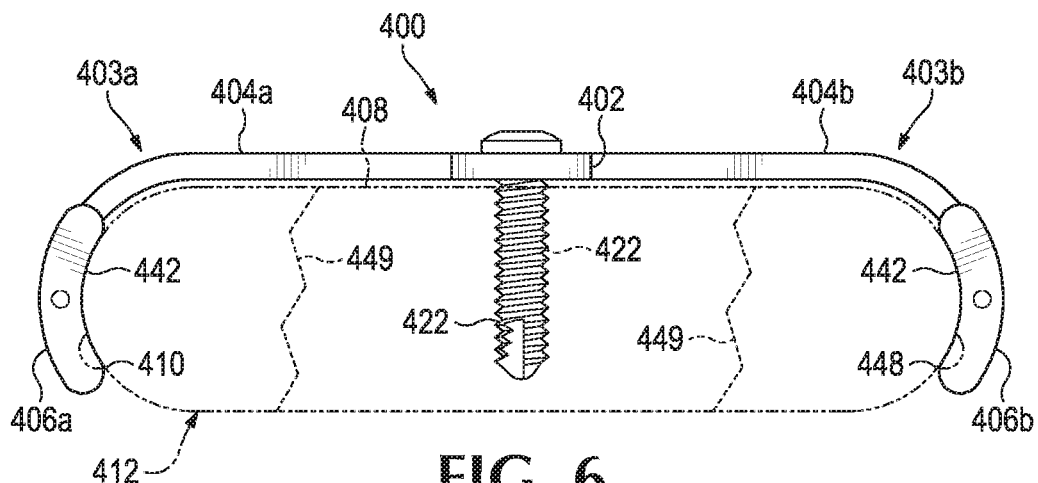
FIG. 6 is an elevation view of yet another implantable device to stabilize bone, where the implantable device is secured to a bone having a pair of fractures, where the implantable device includes a plate, a pair of arms extending in opposite directions from the plate, and a respective buttress member connected to an end of each arm, and where the buttress members have respective bone-engaging surfaces at least generally facing one another.
Figure 6A:
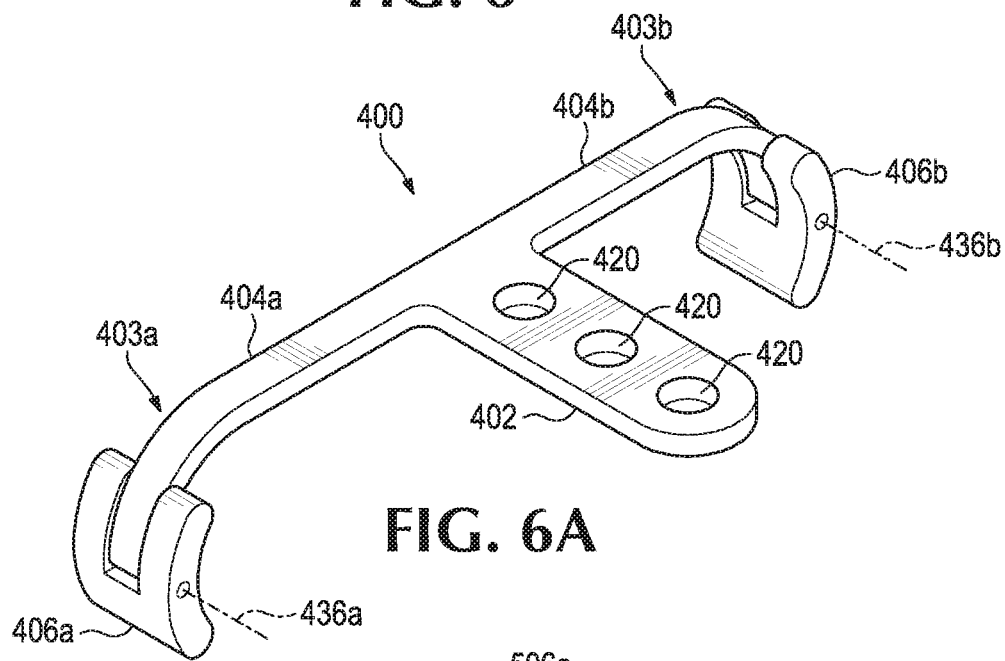
FIG. 6A is an isometric view of the implantable device of FIG. 6 taken in the absence of fasteners and bone.

This example describes an exemplary bone-stabilizing device 400 having a plate 402 and a pair of outriggers 403a, 403b to embrace a bone 412 (or a pair of bones); see FIGS. 6 and 6A.

Plate 402 defines apertures 420 to receive fasteners 422 that secure the plate onto a first bone region 408. Outriggers 403a, 403b provide a pair of arms 404a, 404b extending in opposite lateral directions from plate 402, such that the structure formed collectively by plate 402 and arms 404a, 404b is T-shaped. A buttress member 406a or 406b is pivotably connected to the distal end of each arm 404a, 404b for rotation about a pivot axis 436a or 436b. Each buttress member 406a, 406b contacts a second bone region 410 or a third bone region 448 of bone 412. Bone regions 408, 410, and 448 may be provided by respective fragments of bone 412 created by fractures 449.

Each buttress member 406a, 406b has a bone-engaging surface 442 to engage second bone region 410 or third bone region 448. Each arm 404a, 404b may form a distal bend (e.g., of at least about 90 degrees), such that bone-engaging surfaces 442 of buttress members 406a, 406b face generally toward one another, with buttress members 406a, 406b in their neutral orientations.

Example 4. Device Having a Pair of Adjacent Outriggers

Figure 7:
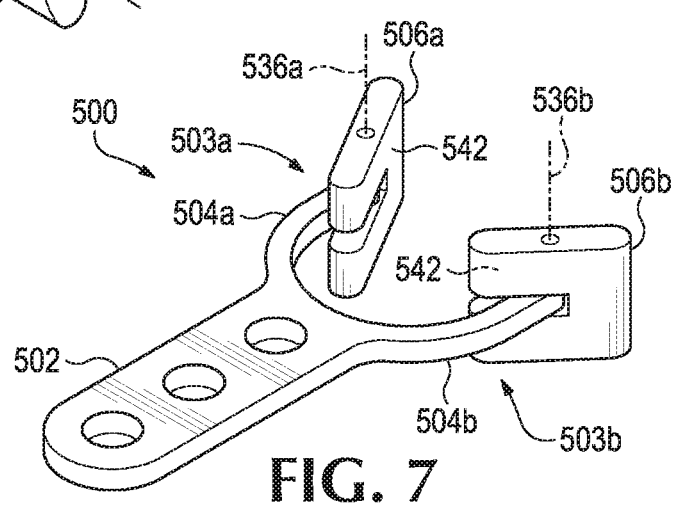
FIG. 7 is an isometric view of still yet another implantable device to stabilize bone, where the implantable device includes a plate, a pair of arms extending from the same end of the plate, and a respective buttress member connected to an end of each arm.

This example describes an exemplary bone-stabilizing device 500 having a plate 502 and a pair of outriggers 503a, 503b extending from an end of plate 502; see FIG. 7.

Outriggers 503a, 503b provide a pair of arms 504a, 504b extending from the same end of plate 502, such that the structure formed collectively by plate 502 and arms 504a, 504b is Y-shaped. A buttress member 506a or 506b is pivotably connected to the distal end of each arm 504a, 504b for rotation about a pivot axis 536a or 536b.

Each buttress member 506a, 506b has a bone-engaging surface 542 to engage a respective bone region. Bone-engaging surfaces 542 of buttress members 506a, 506b are transverse to plate 502, such as generally or substantially orthogonal to plate 502, through the entire pivotal range of each buttress member 506a, 506b.

Example 5. Device Having a Buttress Member with Multi-Plane Pivotability

Figure 8:
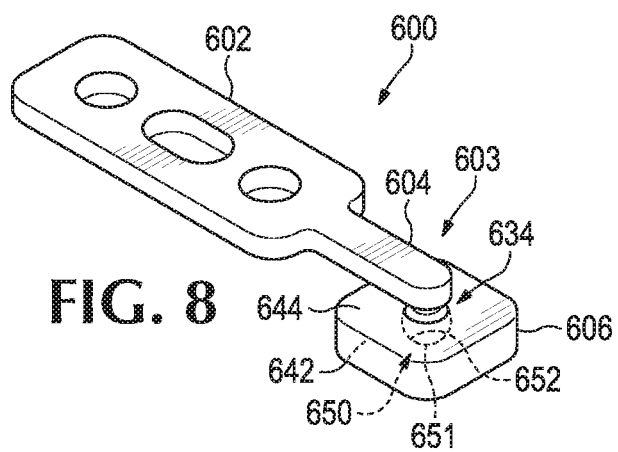
FIG. 8 is an isometric view of another implantable device including a plate, an arm, and a buttress member, where the buttress member is connected to an end of the arm using a ball joint.

This example describes an exemplary bone-stabilizing device 600 having a plate 602 and an outrigger 603 extending axially from an end of plate 602, where outrigger 603 is equipped with an axial arm 604 and a buttress member 606 that is pivotable in each of a plurality of non-parallel planes; see FIG. 8.

Arm 604 and buttress member 606 are connected to one another at a pivotable connection 634 conferring two or more degrees of rotational freedom. In other words, buttress member 606 is pivotable with respect to arm 604 about each of two or more non-parallel pivot axes (and in each of two or more non-parallel planes). In the depicted embodiment, pivotable connection 634 is a ball joint 650 formed by a ball 651 located in a socket 652. Socket 652 is formed opposite a bone-engaging surface 642 of buttress member 606 in an outer surface 644 thereof. The pivotable connection of device 600 may be incorporated into any of the bone-stabilizing devices of the present disclosure, in place of a pivotable connection having only one degree of rotational freedom (i.e., a single pivot axis). However, a pivotable connection defining a single pivot axis can provide sufficient conformation to an engaged bone surface, and can be less expensive to manufacture.

Buttress member 606 is axially offset from plate 602 and located below the plate. Bone-engaging surface 642 is generally or substantially parallel to plate 602, with buttress member 606 in its neutral orientation. However, in other embodiments, the buttress member may be laterally offset from the plate (e.g., see Example 6), and/or at the same elevation as or above the plate. In other embodiments, bone-engaging surface 642 may be oriented transverse to plate 602, such as generally or substantially orthogonal to plate 602, with buttress member 606 in its neutral orientation.

Example 6. Device Having a Pair of Lateral Outriggers

Figure 9:
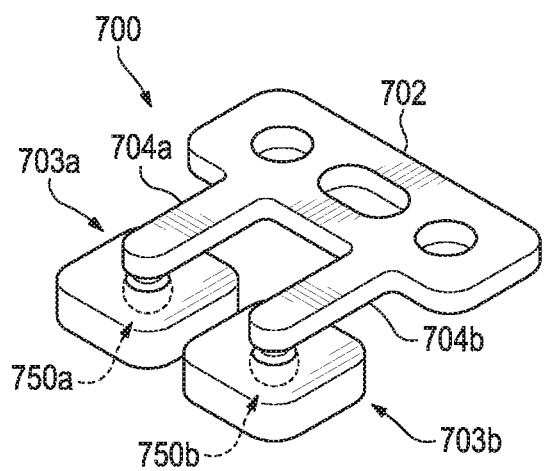
FIG. 9 is an isometric view of an implantable device similar to the device of FIG. 8, except that the device of FIG. 9 has a pair of arms extending laterally and a respective buttress member connected to an end of each arm using a ball joint.

This example describes an exemplary bone-stabilizing device 700 having a plate 702 and a pair of outriggers 703a, 703b each extending laterally from plate 702; see FIG. 9.

Each outrigger 703a, 703b is equipped with a lateral arm 704a or 704b and a buttress member 706a or 706b. A ball joint 750a or 750b of the outrigger connects the lateral arm to the buttress member, for pivotability of the buttress member in multiple non-parallel planes.

Example 7. Device Having a Slidable, Lockable Outrigger

Figure 10:
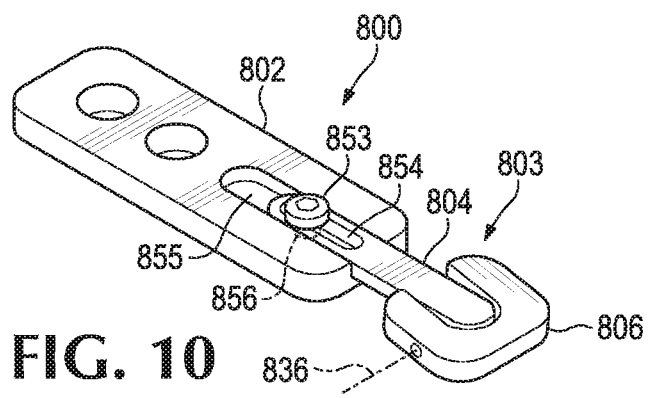
FIG. 10 is an isometric view of yet another implantable device including a plate, an arm, and a buttress member, where the arm is adjustably lockable to the plate to change the distance between the plate and the buttress member.

This example describes an exemplary bone-stabilizing device 800 having a plate 802 and an outrigger 803, where the outrigger has a slidable configuration and a locked configuration; see FIG. 10.

Outrigger 803 has an arm 804 pivotably connected to a buttress member 806, for rotation about a single pivot axis 836. Arm 804 is formed separately from plate 802 and is attached to plate 802 using a fastener, such as a set screw 853 extending through an axial slot 854 defined by arm 804.

Plate 802 defines an elongated recess 855 in which arm 804 can slide. Recess 855 may be formed in a top surface or a bottom surface of plate 802. Recess 855 may have a width that matches that of arm 804, to guide travel of arm 804 with minimal lateral wobble.

Plate 802 also defines an internally-threaded hole 856 in a floor of recess 855, to receive a complementary, externally-threaded shaft portion of set screw 853. Until set screw 853 is tightened against arm 804, the arm is slidable parallel to the long axis of axial slot 854, to continuously adjust the length portion of arm 804 that projects from plate 802, thus adjusting the distance between plate 802 and buttress member 806 (as measured to pivot axis 836). Once tightened, set screw 853 locks arm 804 to plate 802, to fix the length portion of arm 804 that projects from plate 802, thereby fixing the distance between plate 802 and buttress member 806.

Example 8. Device for Pelvic Wall Stabilization

This example describes an exemplary device 900 configured to stabilize the pelvis and having a plate 902 and an outrigger 903; see FIG. 11.

Device 900 is configured to be disposed on a quadrilateral surface of a medial wall of the acetabulum, generally opposite the floor of the acetabulum. Accordingly, the device may be suitable for stabilizing a fractured pelvis having a fracture associated with the acetabulum.

Plate 902 defines a plurality of apertures 920 to receive fasteners to secure the plate onto the pelvis. Each aperture 920 extends through plate 902 between an outer surface 916 and an inner surface 918 thereof.

Outrigger 903 has an arm 904 and a buttress member 906. Arm 904 is formed integrally with plate 902 and projects axially for a short distance from an end thereof. The arm bends sharply (e.g., about 90 degrees) near plate 902 to then follow a path generally or substantially orthogonal to plate 902, along a longitudinal axis 947 of arm 904, to a distal end 930 thereof.

A pivotable connection 934 couples buttress member 906 to arm 904. The pivotable connection may define a single pivot axis 936, as shown, or a pivot point, among others. The pivot axis is parallel to plate 902, such as generally or substantially parallel to the plate. Pivotable connection 934 is centered between opposite edge regions 940a, 940b of buttress member 906, to balance the pressure applied to bone via a bone-engaging surface 942 of buttress member 906. Bone-engaging surface 942 and/or buttress member 906 is transverse to plate 902, such as generally or substantially orthogonal to the plate, with buttress member 906 in its neutral orientation.

Example 9. Device for Stabilization of Acetabular Fragments

This example describes an exemplary bone-stabilizing device 1000 configured to fit at least partway around an acetabular cup on a posterior wall of the pelvis and to stabilize acetabular fragments resulting from fracture, such as comminuted fracture, of the acetabular wall; see FIG. 12.

Device includes a plate 1002 and a series of outriggers 1003 projecting laterally from plate 1002. Plate 1002 may be contoured according to the geometry around the acetabular cup, such that the longitudinal axis of the plate is curved (not shown here). The depicted embodiment has five outriggers 1003 but any suitable number of outriggers may be included. Each outrigger 1003 has an arm 1004 and a buttress member 1006. Each arm 1004 is formed integrally with plate 1002 and projects laterally from a lateral edge thereof. The arm may be linear as shown.

A respective pivotable connection 1034 couples each buttress member 1006 to the corresponding arm 1004. The pivotable connection may define a single pivot axis 1036, as shown, or a pivot point, among others. The pivot axis is at least approximately parallel to plate 1002, such as generally or substantially parallel to the plate. Pivotable connection 1034 is centered between opposite edge regions 1040a, 1040b of each buttress member 1006, to balance the pressure applied to bone via a bone-engaging surface 1042 of the buttress member 1006. Buttress member 1006 is configured to contact bone using a portion proximal to pivotable connection 1034 and another portion distal to pivotable connection 1034. For example, each buttress member 1006 may form a pair of proximal branches 1057 and a distal prong 1058. When installed, the buttress member may pivot about pivot axis 1036 such that one or both proximal branches 1057 and distal prong 1058 contact bone and apply pressure thereto.

Example 10. Device for Stabilization of an Olecranon Fracture

This example describes an exemplary device 1100 configured to stabilize an olecranon fracture 1159 of an ulna 1112 that articulates with a humerus 1160 at a humeroulnar joint; see FIGS. 13 and 14.

Device 1100 includes a plate 1102 and an outrigger 1103, where outrigger 1103 has an arm 1104 projecting from plate 1102 and a buttress member 1106 pivotably connected to a distal end of arm 1104.

FIG. 13 shows plate 1102 secured, using a fastener 1122, to a base 1161 of olecranon 1162 of ulna 1112. Outrigger 1103 spans olecranon fracture 1159, such that the position of a lip portion 1163 of olecranon 1162 is stabilized by pressure applied by buttress member 1106.

Example 11. Device for Stabilization of an Acetabular Region

This example describes an exemplary device 1200 configured to stabilize an acetabular region of a pelvis; see FIG. 15.

Device 1200 includes a plate 1202 and an outrigger 1203. The outrigger has an arm 1204 and a buttress member 1206 pivotably connected to arm 1204. Arm 1204 and buttress member 1206 are coupled to one another via a pivotable connection 1234, which in this case is a ball joint 1250. Arm 1204 extends laterally from plate 1202 to a distal end 1230 of the arm.

Plate 1202 and buttress member 1206 are each configured to be secured to the pelvis with fasteners. More specifically, plate 1202 defines a plurality of apertures 1220 each extending between an outer surface 1216 and an inner surface 1218. Buttress member 1206 defines a plurality of apertures 1264 each extending between bone-engaging surface 1242 and outer surface 1244. The buttress member may be secured to an acetabular region of the pelvis, such that the buttress member extends at least partway around the pelvis, optionally to stabilize acetabular fragments resulting from fracture. In the neutral orientation of buttress member 1206, inner surface 1218 of plate 1202 and bone-engaging surface 1242 of buttress member 1206 face in the same general direction, as shown. In addition, the longitudinal axes defined by plate 1202 and buttress member 1206 are generally parallel to one another.

Example 12. Device for Stabilization of a Rib Cage

Figure 16:
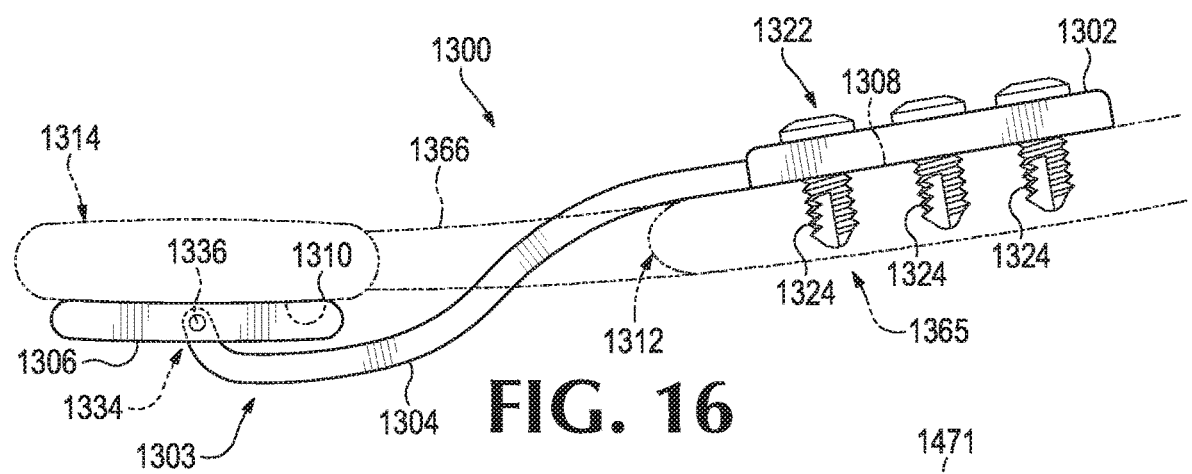
FIG. 16 is a side elevation view of an implantable device including a plate, an arm, and a buttress member, where the device is secured to a rib bone using fasteners and engaged with a posterior surface of a sternum, to stabilize the sternum after surgery for pectus excavatum.

This example describes an exemplary device 1300 configured to stabilize a rib cage 1365, such as a rib cage surgically treated to repair pectus excavatum (i.e., a sunken chest); see FIG. 16.

Device 1300 includes a plate 1302 and an outrigger 1303. The outrigger has an arm 1304 and a buttress member 1306 pivotably connected to one another. Arm 1304 and buttress member 1306 are coupled via a pivotable connection 1334, which in this case defines a single pivot axis 1336 and in other cases permits pivoting about two or more non-parallel axes.

Plate 1302 is secured to an anterior end region 1308 of a rib 1312 of rib cage 1365 using fasteners 1322, which in this case are screws 1324. In other embodiments, plate 1302 may be secured using a different fastener(s), such as one or more sutures.

Buttress member 1306 is engaged with a posterior surface region 1310 of a sternum 1314 of rib cage 1365. Cartilage connecting rib 1312 and sternum 1314 to one another has been resected surgically, leaving only the perichondrium 1366. Buttress member 1306 supports sternum 1314 in a revised position while the cartilage grows back.

In other cases, the cartilage may not be resected surgically in the procedure. Instead, force applied to sternum 1314 via arm 1304 and buttress member 1306 may force sternum 1314 from its initial sunken position to a raised, more anatomical position, while the connecting cartilage remains intact.

Example 13. Device for Stabilization/Expansion of an Articular Region

Figure 17:
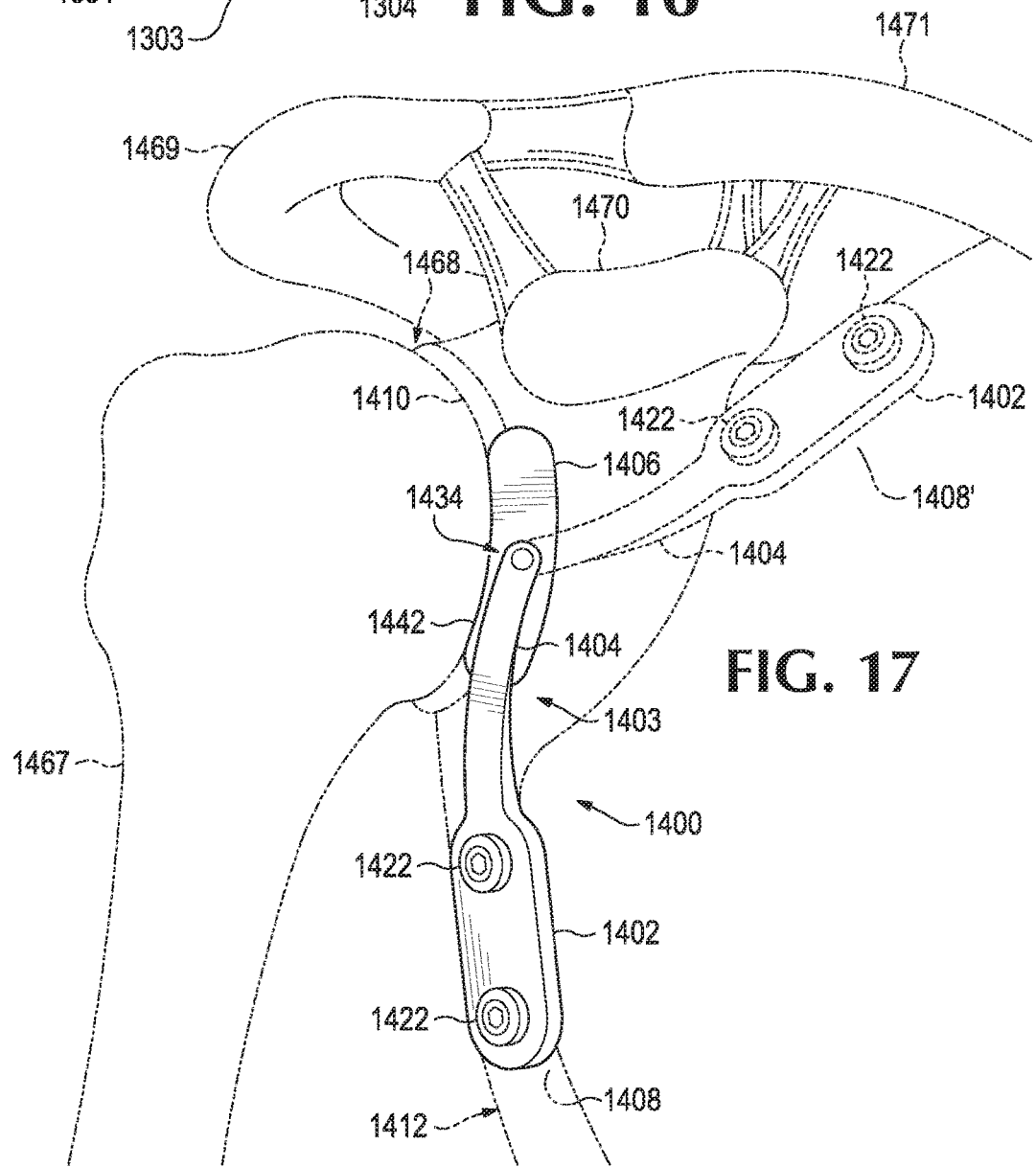
FIG. 17 is a view of an implantable device secured to a scapula using fasteners and stabilizing a Bankart fracture of the glenoid, where the device includes a plate, an arm, and a buttress member, and where the plate is secured in two different, alternative positions on the scapula, with one of the positions shown in dashed outline.

This example describes an exemplary device 1400 configured to stabilize and/or expand an articular region of a bone, such as the glenoid 1410 of a scapula 1412, which articulates with a humerus 1467 at a glenohumeral joint 1468; see FIG. 17.

Device 1400 includes a plate 1402 and an outrigger 1403. The outrigger has an arm 1404 and a buttress member 1406 pivotably connected to one another. Arm 1404 and buttress member 1406 are coupled via a pivotable connection 1434 (e.g., a ball joint), which permits pivoting about two or more non-parallel axes. In other cases, pivotable connection 1434 may define a single pivot axis, as described elsewhere herein.

Plate 1402 may be secured alternatively to different positions on scapula 1412 (acromion 1469, coracoid 1470, and clavicle 1471 are shown for reference). For example, plate 1402 may be secured to a lateral surface region 1408 of scapula 1412, at a position inferior to glenoid 1410, or to a more superior, medial surface region 1408' of scapula 1412, using fasteners 1422, such as screws. These two alternative positions of plate 1402 and arm 1404 are shown respectively in solid lines and dashed lines.

Buttress member 1406 is located against glenoid 1410 at the same position, for each depicted position of plate 1402. The buttress member may stabilize a Bankart fracture (i.e., a fracture of the glenoid rim), may function as an impediment to anterior dislocation of the head of humerus 1467 from glenohumeral joint 1468, and/or may articulate with the head of humerus 1467 to extend the glenoid rim. Accordingly, buttress member 1406 may have a bone-engaging surface 1442 suitable for articulation. For example, bone-engaging surface 1442 (and/or buttress member 1406) may be formed of polymer or cobalt chrome, among others.

Example 14. Device for Stabilization of a Proximal Tibia

This example describes an exemplary device 1500 configured to stabilize a fractured proximal tibia 1512; see FIGS. 18, 18A, and 18B. (A femur 1572 and a fibula 1572a are shown for reference.)

Device 1500 includes a plate 1502 and an outrigger 1503. The outrigger has an arm 1504 and a buttress member 1506 pivotably connected one another. Arm 1504 and buttress member 1506 are coupled via a pivotable connection 1534 (e.g., a ball joint), which permits pivoting about two or more non-parallel axes. In other cases, pivotable connection 1534 may define a single pivot axis, as described elsewhere herein.

Plate 1502 is secured to a medial region 1508 of proximal tibia 1512 using fasteners 1522, such as screws. The plate may (or may not) bridge a fracture of proximal tibia 1512.

Arm 1504 is formed separately from plate 1502. The arm and plate are connected to one another at an adjustable joint 1573 including a set screw 1574. Joint 1573 is adjustable between movable and locked configurations by tightening or loosening set screw 1574. In the movable configuration, arm 1504 is pivotable about a pivot axis 1575 that is orthogonal to plate 1502, to change the orientation of the arm. In the locked configuration, the orientation of arm 1504 is fixed. Set screw 1574 may extend through a circular aperture (i.e., the movable configuration is only a pivotable configuration) or through an elongated aperture (i.e., a slot) defined by arm 1504. The use of a slot permits arm 1504 to pivot and slide in the movable configuration, to adjust a length portion of the arm that projects from an edge of plate 1502 and/or to adjust a distance between plate 1502 and buttress member 1506.

Arm 1504 bridges a fracture 1576 of proximal tibia 1512 that forms a tibial fragment 1510. Fracture 1576 may, for example, be a lateral condyle fracture, which extends to the tibial plateau, as shown. In other cases, fracture 1576 may be a medial condyle fracture, and plate 1502 may be secured more laterally on the fractured proximal tibia 1512.

Buttress member 1506 applies pressure to tibial fragment 1510 created by fracture 1576. The buttress member has a bone-engaging surface 1542 opposite an outer surface 1544. Bone-engaging surface 1542 defines a plurality of spikes 1577. The spikes project from a body 1578 of buttress member 1506 and resist slippage of the buttress member on tibial fragment 1510.

Example 15. Device for Stabilization of a Proximal Femur

Figure 19:
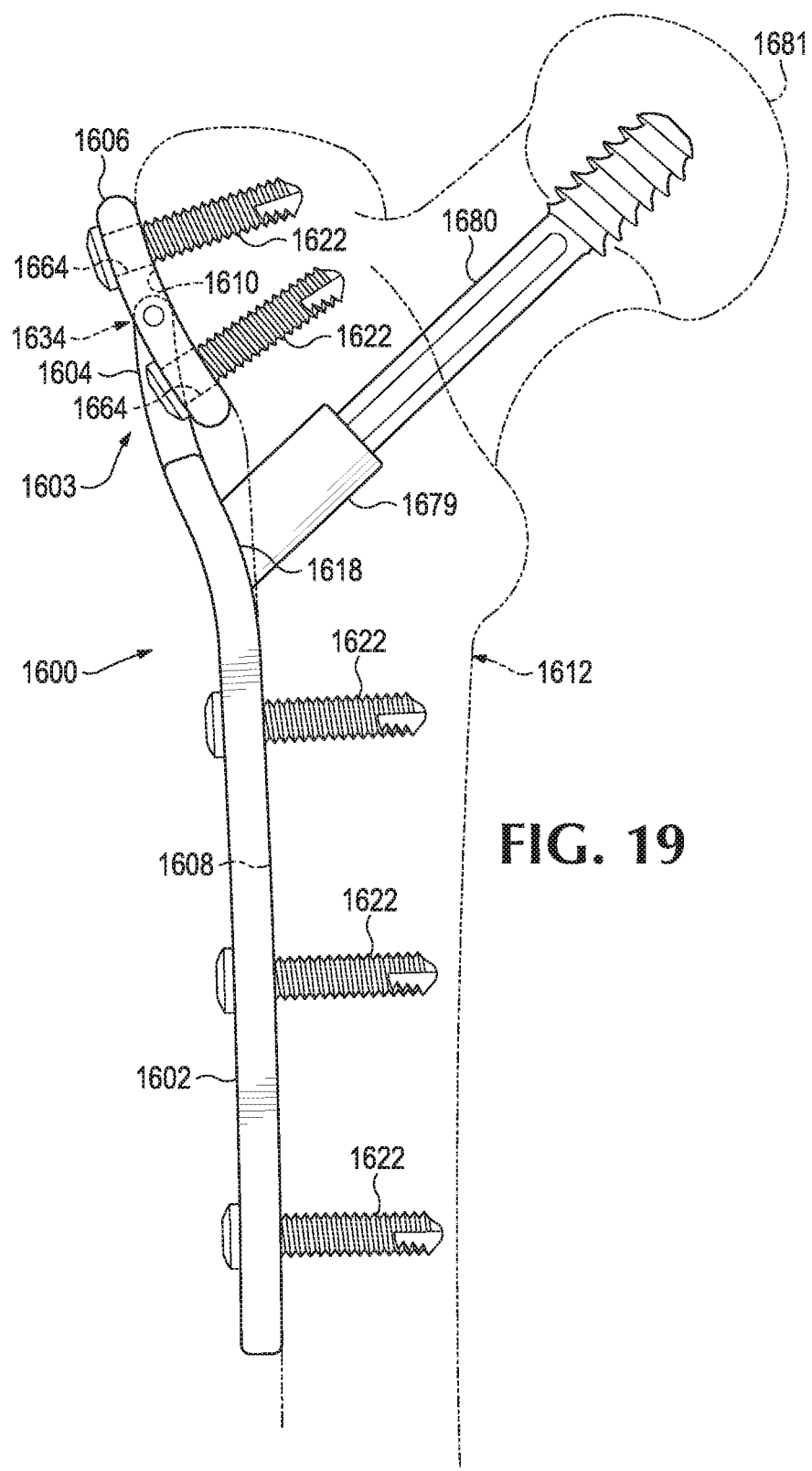
FIG. 19 is a side view of an implantable device secured to a fractured proximal femur, where the device includes a plate, an arm, and a buttress member, and where the device also includes a barrel projecting from an inner surface of the plate and a hip screw extending from and slidable in the barrel.

This example describes an exemplary device 1600 configured to stabilize a fractured proximal femur 1612; see FIG. 19.

Device 1600 includes a plate 1602 and an outrigger 1603 having an arm 1604 and a buttress member 1606. Plate 1602 is located on a lateral shaft region 1608 of proximal femur 1612 and secured with fasteners 1622.

Arm 1604 projects axially from plate 1602 to a pivotable connection 1634 with buttress member 1606. The pivotable connection defines a pivot axis and allows buttress member 1606 to conform to the local orientation of an end region 1610 of proximal femur 1612 by rotation about the pivot axis. End region 1610 of proximal femur 1612 is located laterally, but more proximally than lateral shaft region 1608. Buttress member 1606 defines apertures 1664 to receive fasteners, such as screws, to secure the buttress member to bone. Alternatively, buttress member 1606 may not be secured to proximal femur 1612 with fasteners, independently of plate 1602, and apertures 1664 may be omitted or may be present but not used.

Device 1600 also may include a barrel 1679 and a sliding screw 1680. Barrel 1679 projects from an inner surface 1618 of plate 1602 and is located in proximal femur 1612 when implanted, as shown. Sliding screw 1680 has a trailing end located slidably in barrel 1679, to permit barrel 1679 and sliding screw 1680 to move relative to one another, in a direction parallel to the long axis of sliding screw 1680. The sliding screw extends through a femoral neck and into a femoral head 1681, where an external thread of sliding screw 1680 anchors the sliding screw in femoral head 1681.

Example 16. Device for Stabilization of a Proximal Ulna and Radius

Figure 20:
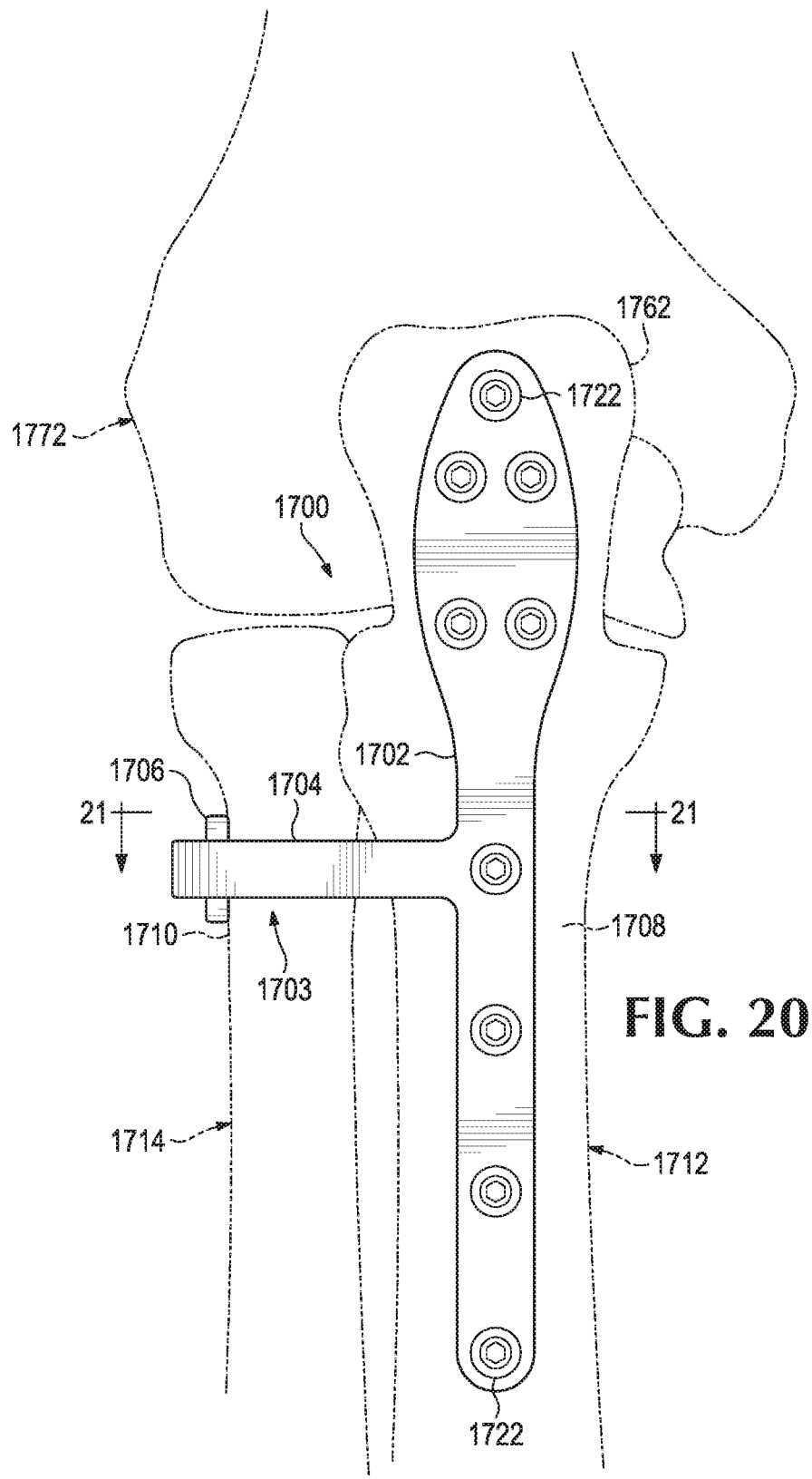
FIG. 20 is a top plan view of an implantable device attached to the proximal forearm, where the device includes a plate secured to the proximal ulna and a buttress member engaged with the proximal radius.
Figure 21:
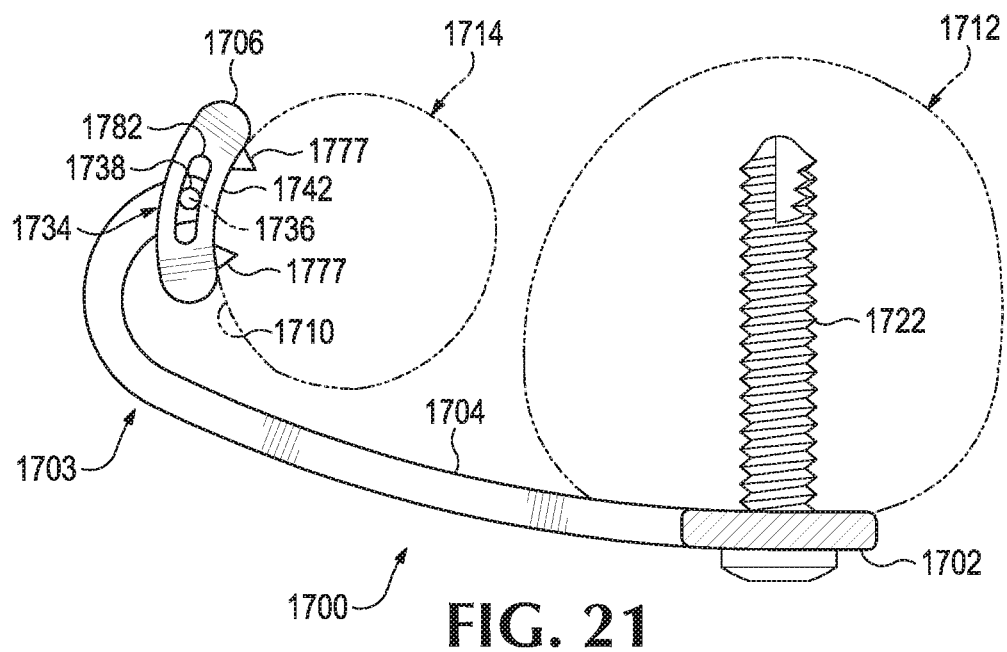
FIG. 21 is a sectional view of the device and bones of FIG. 20, taken generally along line 21-21 of FIG. 20.

This example describes an exemplary device 1700 configured to stabilize a proximal ulna 1712 and a proximal radius 1714 relative to one another; see FIGS. 20 and 21. (A distal humerus 1772 that articulates with proximal ulna 1712 and proximal radius 1714 is shown for reference.)

Device 1700 includes a plate 1702 and an outrigger 1703. The outrigger has an arm 1704 and a buttress member 1706 pivotably connected to one another via a pivotable connection 1734 (see FIG. 21).

Plate 1702 is secured to a posterior region 1708 of proximal ulna 1712 using fasteners 1722. The plate may overlap both a shaft region and the olecranon 1762 of proximal ulna 1712 and may fix a fracture of proximal ulna 1712.

Arm 1704 projects laterally from plate 1702 and proximal ulna 1712 to a position adjacent a lateral region 1710 of proximal radius 1714.

Buttress member 1706 has a bone-engaging surface 1742 to apply pressure to lateral region 1710 of proximal radius 1714. Bone-engaging surface 1742 has spikes 1777 to engage lateral region 1710 and resist slippage.

Pivotable connection 1734 permits buttress member 1706 to pivot and slide with respect to arm 1704. A pivot axis 1736 is defined by a pin 1738 that is mounted to arm 1704. Buttress member 1706 defines a slot 1782 is which pin 1738 is located. Pin 1738 is slidable along slot 1782 to move pivot axis 1736 with respect to buttress member 1706. Slot 1782 may be arcuate to guide pin 1738 along a curved path, which permits proximal radius 1714 to rotate about its long axis, and thus the corresponding forearm to be rotated by a subject after device 1700 is implanted, to produce pronation and supination.

Example 17. Device with Discretely Adjustable Outrigger

Figure 22:
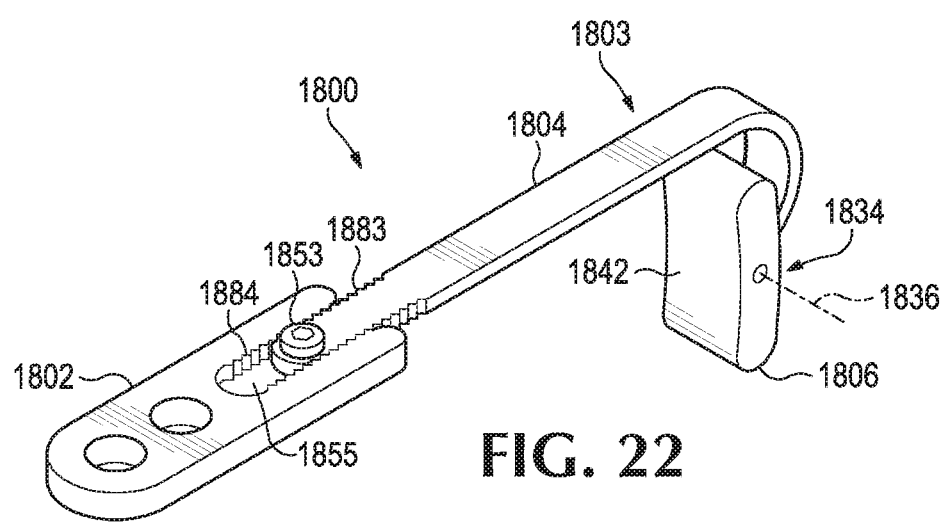
FIG. 22 is an isometric view of an implantable device including a plate, an arm, and a buttress member, where an axial position of the arm with respect to the plate is adjustable and lockable.

This example describes an exemplary device 1800 configured to stabilize bone and including a plate 1802 and an outrigger 1803 having an arm 1804 that is lockable at each of a series of discrete positions with respect to the plate 1802; see FIG. 22.

Device 1800 has similarity to device 300 of Example 2, particularly the shape of the distal portion of outrigger 1803 (compare with FIG. 5), and to device 800 of Example 7, particularly the slidable, lockable capabilities of arm 1804 of outrigger 1803 (compare with FIG. 10).

Arm 1804 is pivotably connected to a buttress member 1806. A proximal end of arm 1804 has a serrated portion 1883 that is complementary to a recess 1855 having a serrated wall 1884. Serrated portion 1883 of arm 1804 fits into recess 1855 at series of uniformly spaced positions along recess 1855 at which teeth of serrated portion 1883 are aligned with indentations defined by serrated wall 1884. Arm 1804 is lockable at each of the uniformly spaced positions by tightening a set screw 1853, which threads into an internally-threaded hole defined in the floor of recess 1855, similar to device 800 of Example 7.

Buttress member 1806 is coupled to arm 1804 at a pivotable connection 1834 defining a pivot axis 1836. Pivot axis 1836 may be generally or substantially parallel to plate 1802. A bone-engaging surface 1842 of buttress member 1806 faces generally toward plate 1802, as in device 300 of Example 2.

Figure 23:
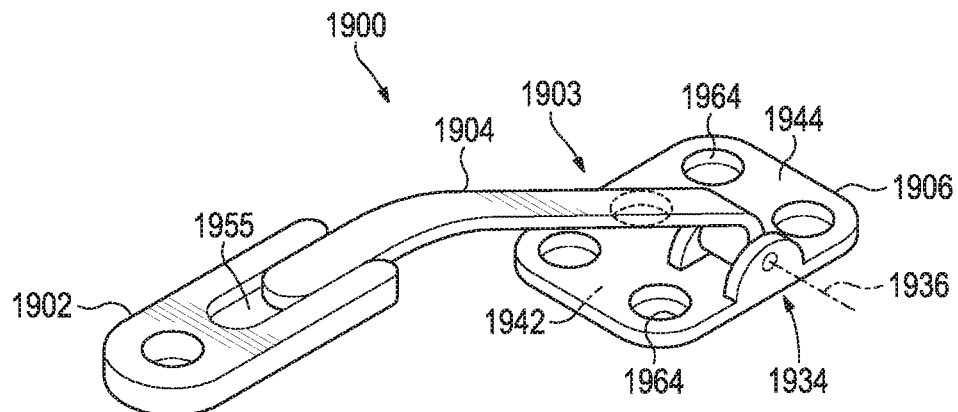
FIG. 23 is an isometric view of another implantable device including a plate, an arm, and a buttress member, where an axial position of the arm with respect to the plate is adjustable and lockable.

Example 18. Device with an Adjustable Outrigger Having a Securable Buttress Member This example describes an exemplary device 1900 configured to stabilize bone. Device 1900 includes a plate 1902 and an outrigger 1903 that is translationally adjustable with respect to plate 1902. Outrigger 1903 is equipped with a fastener-securable buttress member 1906; see FIG. 23.

Outrigger 1903 has an arm 1904 pivotably connected to buttress member 1906. A proximal end of arm 1904 is slidable in a recess 1955 formed in an outer surface of plate 1902, and is lockable to plate 1902, such as with a set screw (also see Examples 7 and 17).

Buttress member 1906 is coupled to arm 1904 at a pivotable connection 1934 for pivotal motion about a single pivot axis 1936. A plurality of apertures 1964 to receive fasteners are defined by buttress member 1906 between a bone-engaging surface 1942 and an outer surface 1944.

Example 19. Device with an Adjustable Outrigger

Figure 24:
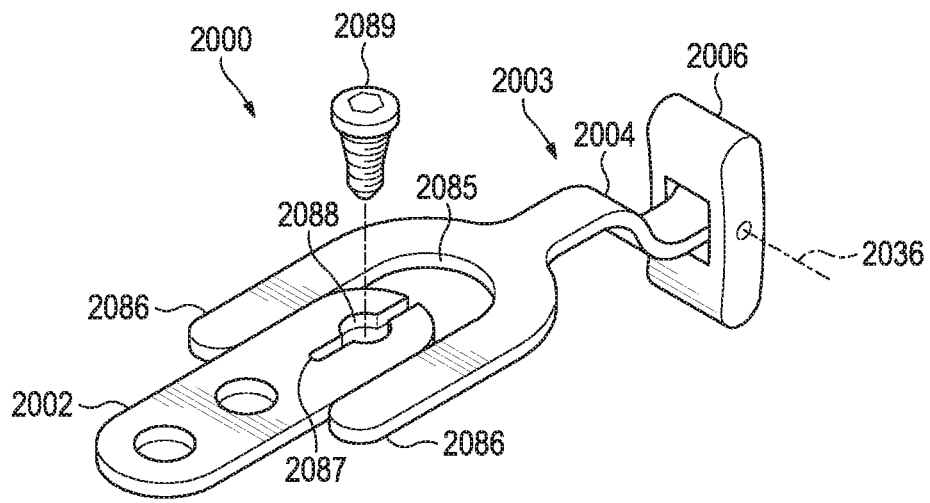
FIG. 24 is an isometric view of yet another implantable device including a plate, an arm, and a buttress member, where an axial position of the arm with respect to the plate is adjustable and lockable.

This example describes an exemplary device 2000 configured to stabilize bone and including a plate 2002 and an outrigger 2003 that is translationally adjustable with respect to plate 2002; see FIG. 24.

Outrigger 2003 has an arm 2004 pivotably connected to a buttress member 2006, for pivotal motion about a pivot axis 2036. A proximal end of arm 2004 defines an opening 2085 sized to match the width of an end portion of plate 2002. Opening 2085 may be defined between a pair of branches 2086. Plate 2002 has a split end 2087 including a hole 2088 to receive a tapered set screw 2089. As set screw 2089 is advanced into hole 2088, split end 2087 is expanded by the set screw to lock arm 2004 to plate 2002.

Example 20. Clavicle Hook Device

This example describes devices and methods for stabilizing a clavicle and/or an acromioclavicular joint; see FIGS. 25-42. However, these devices and methods may be applied to any suitable bone(s) and/or joint.

i. Summary

An exemplary device may comprise a plate configured to be secured onto a superior surface region of the clavicle. The device also may comprise an outrigger providing a hook and including an arm extending from the plate and a discrete, pivotably-connected buttress member forming a tip of the hook. The buttress member may be configured to be placed against an inferior surface region of an acromion of the acromioclavicular joint, and may be self-orienting in response to contact with the acromion, to improve alignment of the buttress member with the acromion surface. The buttress member may be pivotably connected to the arm at a position spaced from a transverse portion of the arm.

ii. Background

A shoulder girdle attaches each upper limb to the axial skeleton. The shoulder girdle is composed of two bones in humans, clavicle c (or collarbone) and scapula s (or shoulder blade) (see FIG. 25).

Clavicle c is located on the anterior side of the shoulder girdle. This bone links scapula s to the sternum (or breastbone). More specifically, clavicle c articulates with the sternum medially at a sternoclavicular joint, and with scapula s laterally at an acromioclavicular joint ac. Joint ac is formed between the lateral end of the clavicle and acromion a of scapula s. Acromion a is an anterior process formed by a superior region of scapula s.

Trauma to the shoulder girdle can fracture clavicle c near its lateral end, and/or tear acromioclavicular soft tissue st that attaches the lateral end of clavicle c to scapula s at acromion a. These injuries are often treated by implanting a clavicle hook plate, such as device d, to fix clavicle c and/or repair a dislocation at joint ac.

Figure 25:
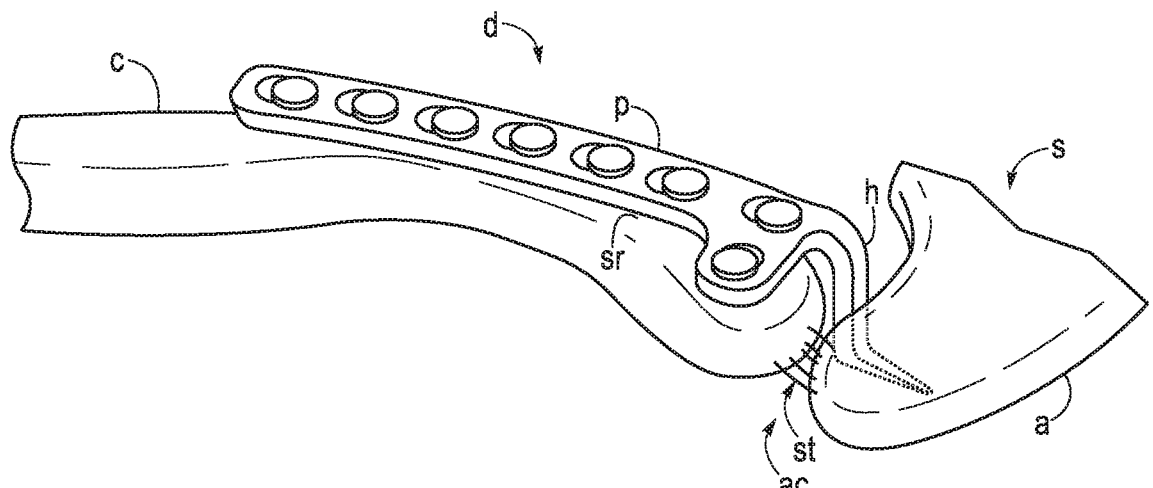
FIG. 25 is a fragmentary view of a left shoulder girdle, particularly a clavicle and an acromion articulating with one another at an acromioclavicular (AC) joint, taken with a device (a clavicle hook plate) of the prior art secured on the clavicle and stabilizing the AC joint.
Figure 26:
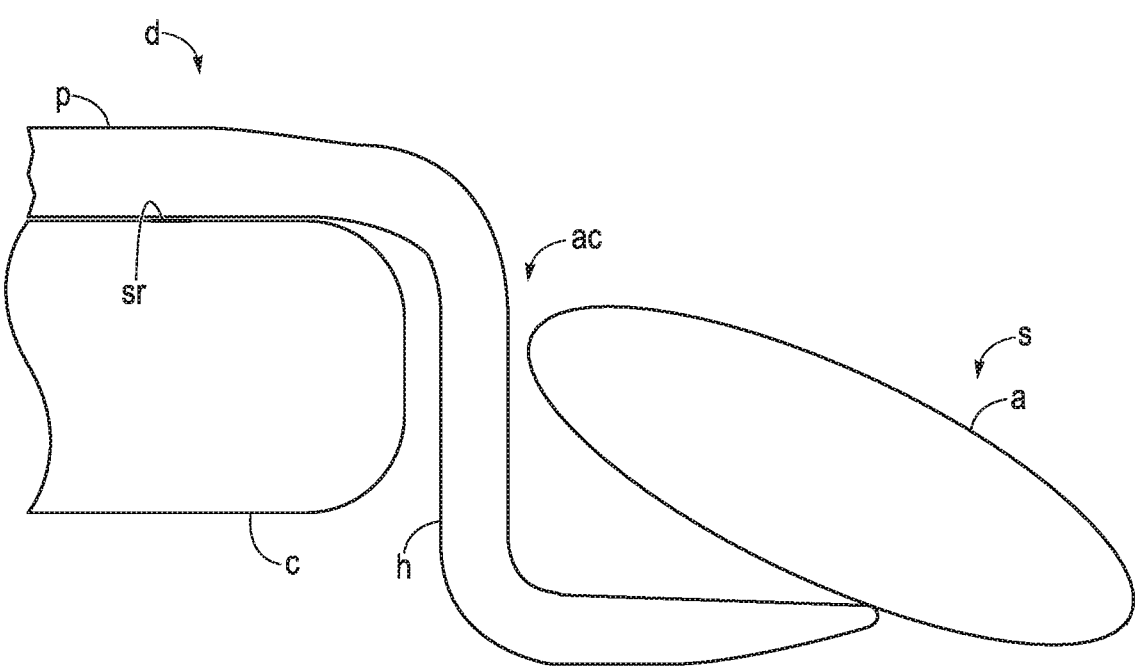
FIG. 26 is a fragmentary side view of the device of FIG. 25 stabilizing the AC joint, taken with the clavicle and acromion represented more schematically, and illustrating how the hook of the device may point-load and erode the acromion.

Device d has a mounting plate p and a hook h (see FIGS. 25 and 26). Mounting plate p forms an elongated shaft and an enlarged head. The shaft and the head each define apertures to receive fasteners, such as bone screws, that secure mounting plate p onto a superior surface region sr of clavicle c. Each aperture extends through mounting plate p, between a top surface and a bottom surface thereof.

Hook h is formed integrally with mounting plate p. The hook extends from a head of mounting plate p to a distal end (see FIG. 26). Once implanted, device d spans a gap between clavicle c and acromion a, at a position posterior to joint ac, and contacts an inferior surface region of acromion a (see FIGS. 25 and 26). In this configuration, device d can maintain the articular ends of clavicle c and acromion a near one another as clavicle c and/or associated acromioclavicular soft tissue st heals, while permitting some needed motion around joint ac.

Device d provides stabilization and promotes an early return to mobilization. However, significant complications connected to use of device d have been reported, including pain and irritation, and, more significantly, erosion of acromion a. A leading explanation for these complications blames point loading of acromion a using the distal end of hook h (see FIG. 26).

This point loading can be challenging to avoid. The surgical approach used by surgeons when device d is implanted does not allow visual access to the underside of acromion a. Accordingly, the surgeon cannot readily determine whether the elongated distal portion of hook h is arranged parallel to the inferior surface region of acromion a, to minimize point loading, or forms a significant angle with the acromion surface, to create point loading (as in FIG. 26).

Modifications to device d attempt to provide a better fit under acromion a. These modifications include forming mounting plate p and hook h separately from one another, to permit adjustment of the hook's orientation and/or shape. However, these modified devices fail to consistently overcome problems with point loading of the acromion, presumably due to the surgeon's inability to visually check whether the hook is properly aligned with the acromion. Improved clavicle hook plates are needed.

iii. Devices for Acromioclavicular Stabilization

This example describes exemplary devices for stabilizing a clavicle, an acromion, and/or an acromioclavicular joint; see FIGS. 27-42.

FIGS. 27-35 show a device 2100 including a mounting plate 2102 (interchangeably called a plate) and an outrigger 2103, wherein the outrigger forms a hook. The outrigger has an arm 2104 and a buttress member 2106 pivotably connected to a distal end of arm 2104.

Plate 2102 may have any combination of features described above for device d in the preceding subsection. For example, plate 2102 may include an elongated shaft 2107 and a head 2109 that is continuous with shaft 2107 (see FIGS. 27 and 28). Head 2109 may or may not be enlarged in width with respect to an adjacent end of shaft 2107 (compare FIGS. 25 and 28).

Plate 2102 has a top surface 2116 (an outer surface) and a bottom surface 2118 (an inner surface). The plate defines a plurality of apertures 2120 to receive fasteners (see FIG. 27). Apertures 2120 extend through plate 2102 between top surface 2116 and bottom surface 2118. The apertures may include any combination of circular apertures 2111a, slots 2111b, and pin/wire/suture-receiving holes 2111c.

Figure 28:
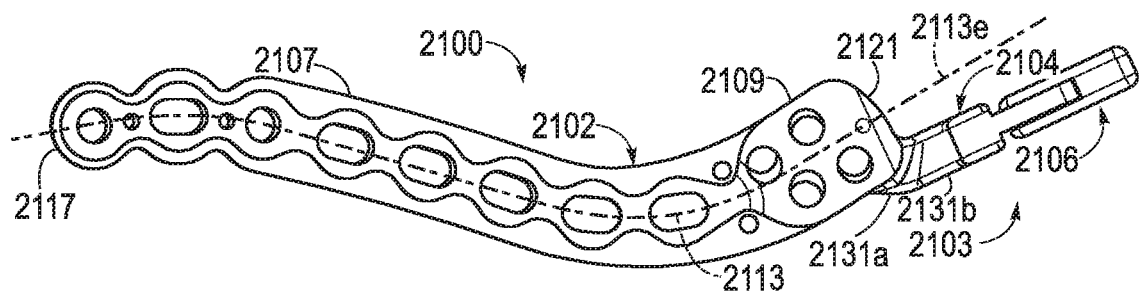
FIG. 28 is a bottom view of the device of FIG. 27.
Figure 29:
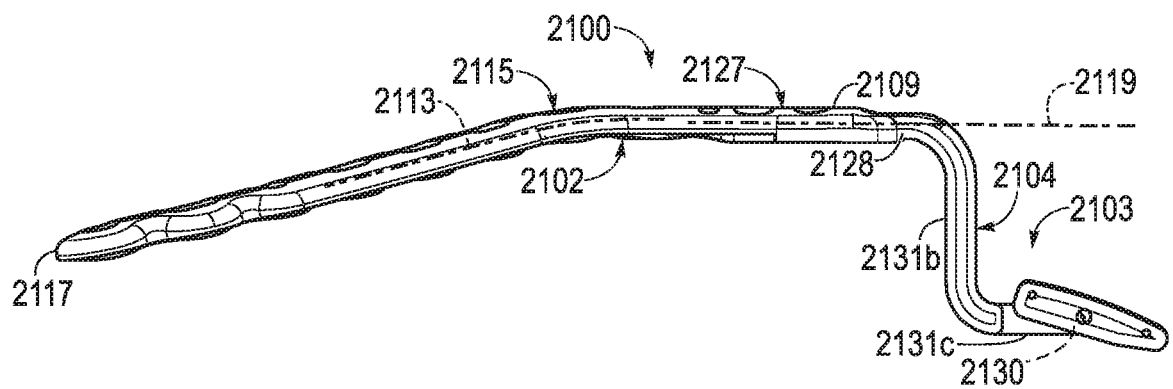
FIG. 29 is a side view of the device of FIG. 27.

Plate 2102 may define a longitudinal axis 2113 that is nonlinear, as shown in FIGS. 28 and 29. More particularly, plate 2102 may be precontoured to fit onto a superior surface region of the clavicle. Accordingly, plate 2102 may have curvature as it extends along a non-linear longitudinal axis 2113 away from outrigger 2103. Optionally, plate 2102 may have curvature in opposite directions (posterior and anterior), as shown in FIG. 28, to produce a double-curved (generally S-shaped) configuration, if plate 2102 is configured to extend along more than one-half of the length of the clavicle. Plate 2102 also may have an inferior bend, indicated at 2115 in FIG. 29, as the plate extends away from outrigger 2103 toward a shaft end 2117 of plate 2102. Head 2109 may define a plane 2119 near a head end 2121 of plate 2102 (see FIGS. 28 and 29).

Figure 27:
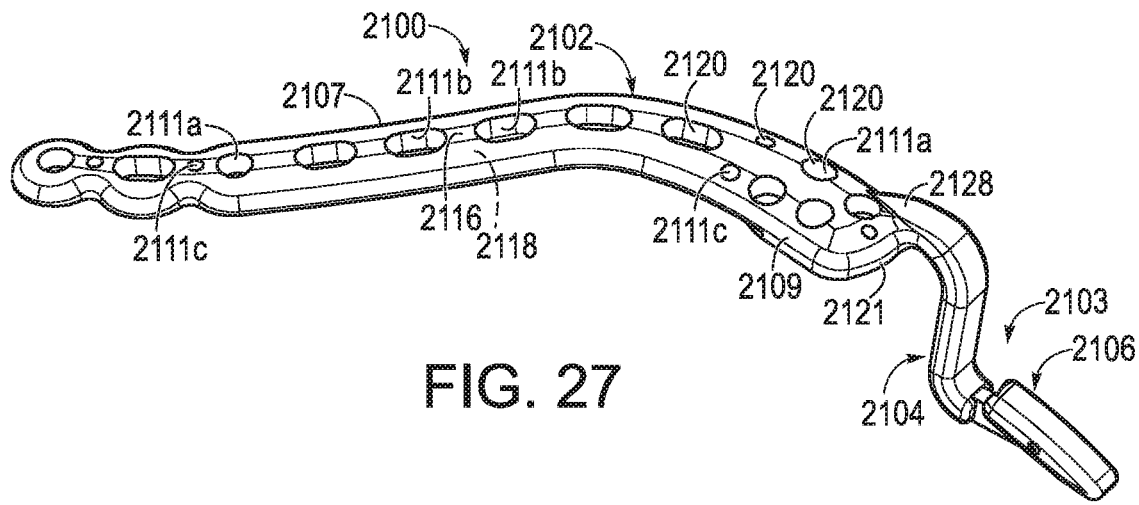
FIG. 27 is a view of an exemplary device for stabilizing a clavicle and/or an AC joint, where the device includes a plate and an outrigger providing a hook, and where the outrigger has an arm formed integrally with the plate, and a discrete, pivotably-connected, self-orienting buttress member forming a tip of the hook and configured to engage the acromion.
Figure 32:
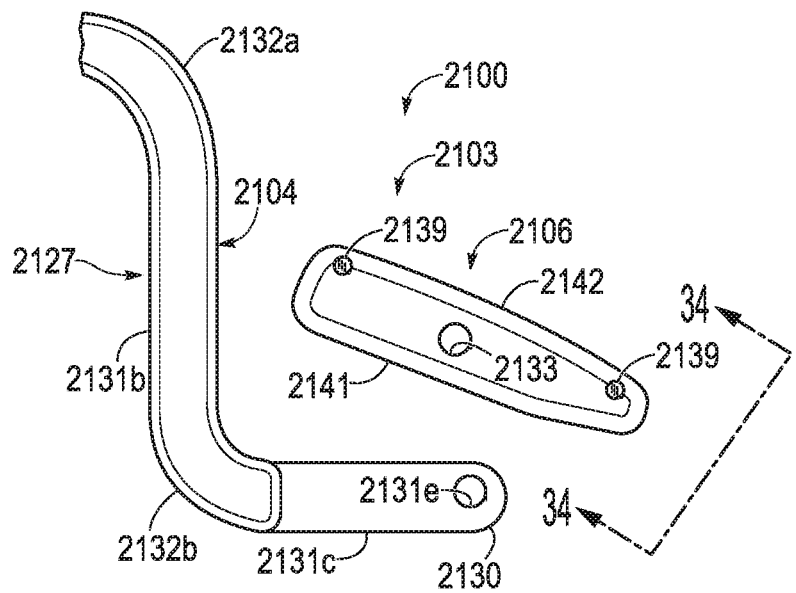
FIG. 32 is another fragmentary side view of the device of FIG. 27, taken generally as in FIG. 31 but with the buttress member exploded from the arm.
Figure 33:
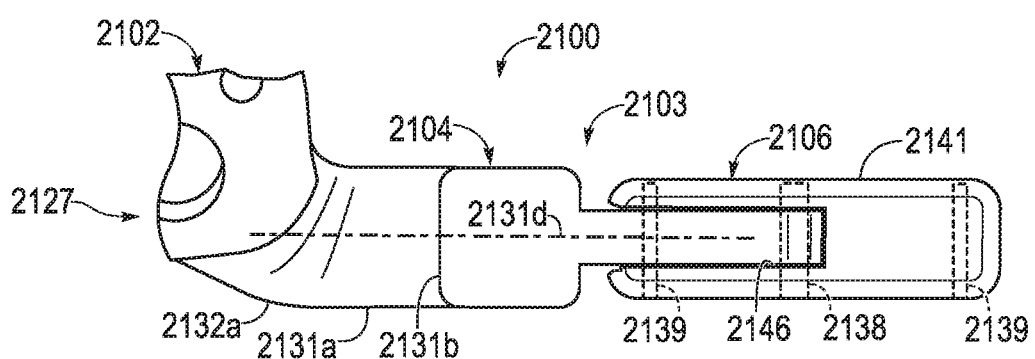
FIG. 33 is a fragmentary bottom view of the device of FIG. 27, taken generally around the outrigger along line 33-33 of FIG. 30.
Figure 34:
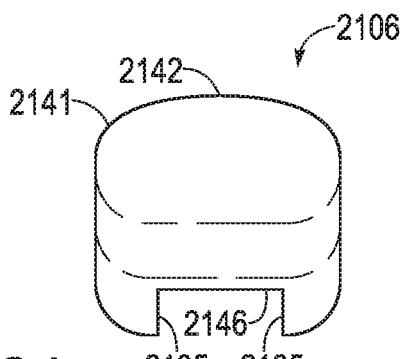
FIG. 34 is an end view of the buttress member of the device of FIG. 27, taken in isolation along line 34-34 of FIG. 32.

Outrigger 2103 is not one piece, in contrast to hook h of device d (see FIGS. 27, 32, and 33; compare with FIGS. 25 and 26). Instead, outrigger 2103 has an arm 2104 and a buttress member 2106 that are formed separately from one another. (Buttress member 2106 interchangeably may be called a tip or endpiece of the hook.)

Figure 30:
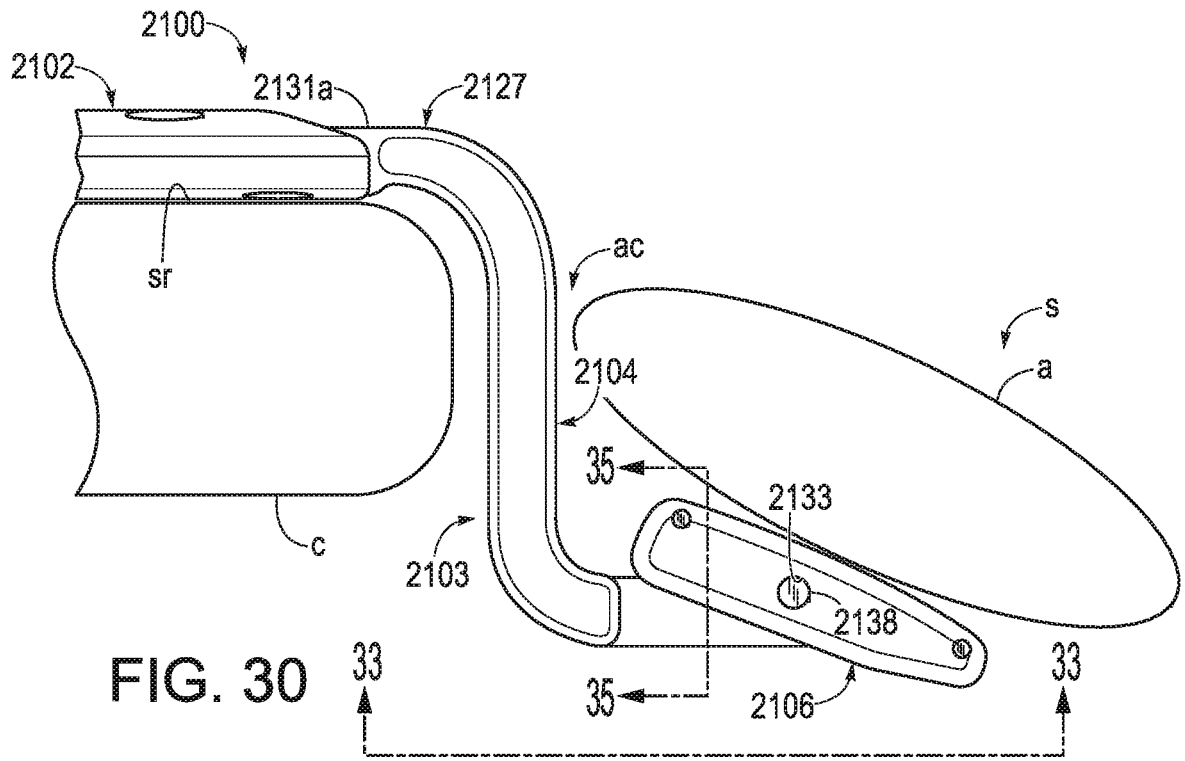
FIG. 30 is a fragmentary side view of the device of FIG. 27, taken with the device spanning a schematic AC joint.

Arm 2104 and plate 2102 may be formed by the same unitary component 2127 of device 2100 (see FIGS. 28-30). The adjective "unitary" means that the unitary component has no discrete parts that are movable relative to one another. Accordingly, arm 2104 and plate 2102 may be formed integrally with one another (i.e., as one piece), or may be formed as separate pieces that are nonremovably attached to one another (e.g., welded or bonded).

Figure 31:
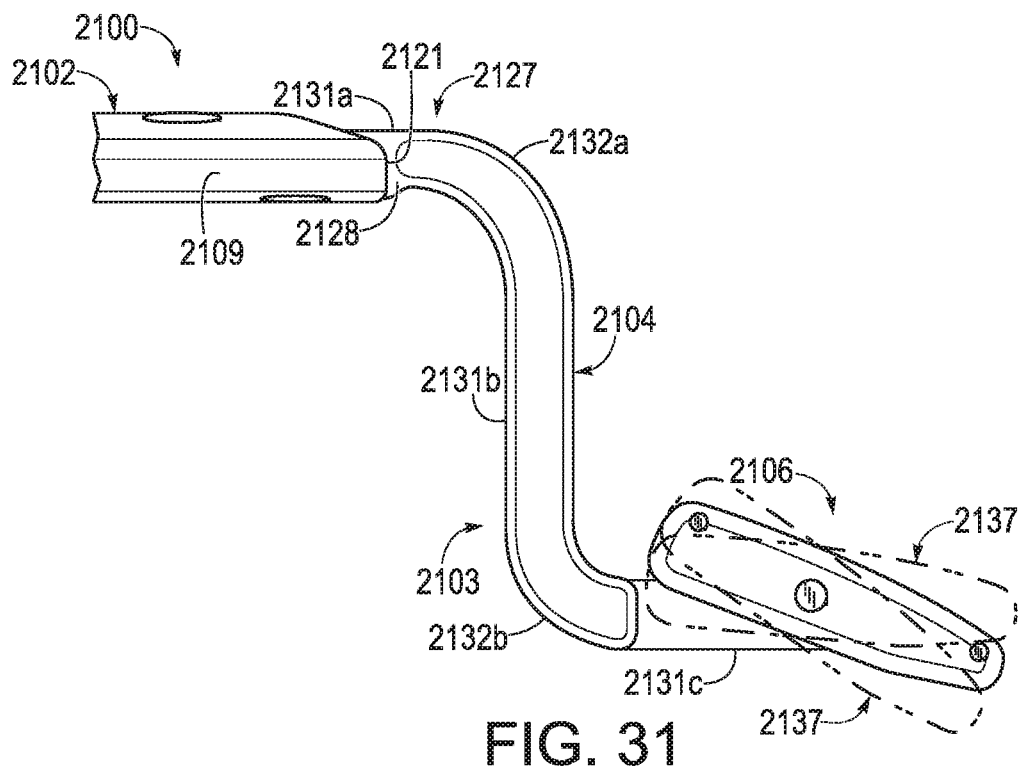
FIG. 31 is a fragmentary side view of the device of FIG. 27, taken generally as in FIG. 30 but in the absence of bone, and illustrating pivotal motion of the buttress member that permits the buttress member to have an orientation that is self-adjusting in response to contact with the acromion, for an improved fit of the device.

Arm 2104 extends from a proximal end 2128 at plate 2102, to a distal end 2130 that is spaced from plate 2102 and plane 2119 (see FIGS. 29, 31, and 32). Distal end 2130 may be offset longitudinally and transversely below plate 2102. Arm 2104 may include a proximal portion 2131$a$ (including proximal end 2128), a transverse portion 2131$b$, and a distal portion 2131$c$ (including distal end 2130).

Proximal portion 2131$a$ may project from head 2109 near or at head end 2121 of plate 2102 (see FIG. 31). For example, in the depicted example, proximal end 2128 extends from a posterior side of head 2109 at head end 2121 (see FIG. 27). Proximal portion 2131$a$ may extend generally along a tangential extension 2113$e$ of longitudinal axis 2113 from head 2109, such as within about 20 degrees of parallel to the tangential extension, for any suitable distance (see FIG. 28). Accordingly, proximal portion 2131$a$ may or may not be elongated. In some examples, proximal portion 2131$a$ may be omitted, such that transverse portion 2131$b$ projects directly from plate 2102 and provides proximal end 2128 of arm 2104.

Transverse portion 2131$b$ may be elongated transverse to plate 2102 and transverse to an elongated distal portion 2131$c$ of arm 2104 (see FIGS. 29 and 32). The term "transverse," as used herein, means oriented at an angle of 45-135 degrees with respect to a given structure, such as at 60-120, 80-125, 85-120, 85-95, or 90 degrees relative to the structure. For example, transverse portion 2131$b$ is transverse to plate 2102 of device 2100 and to distal portion 2131$c$ of arm 2104 because the transverse portion is substantially orthogonal to plane 2119 and to a longitudinal axis defined by distal portion 2131$c$. In other examples, transverse portion 2131$b$ may form an angle of 85-95 degrees with plate 2102 and an angle of 85-125 degrees with distal portion 2131$c$.

Distal portion 2131$c$ may have any suitable features. For example, distal portion 2131$c$ may be narrower in width than transverse portion 2131$b$, when width is measured normal to a plane 2131$d$ defined collectively by transverse portion 2131$b$ and distal portion 2131$c$ (see FIGS. 33 and 35). A hole 2131$e$ may be defined by distal portion 2131$c$, optionally at distal end 2130 (see FIG. 32). Distal end 2130 may be rounded.

Arm 2104 may form a proximal bend 2132$a$ and/or a distal bend 2132$b$ (see FIG. 32). Each bend 2132$a$, 2132$b$ may be a rounded bend (as shown), or at least one of the bends may be a sharp bend. Proximal bend 2132$a$ may be formed between proximal portion 2131$a$ and transverse portion 2131$b$ (or between transverse portion 2131$b$ and plate 2102). Distal bend 2132$b$ may be formed between transverse portion 2131$b$ and distal portion 2131$c$, and interchangeably may be called a connecting bend. Transverse portion 2131$b$ and/or one or both bends 2132$a$, 2132$b$ may have a width measured normal to plane 2131$d$ of arm 2104, and a thickness measured parallel to plane 2131$d$. In some embodiments, the width may be greater than the thickness, such as at least twice the thickness. In other embodiments, the width and the thickness may be the same or the width may be less than the thickness.

Buttress member 2106 may have any suitable structure and connection to arm 2104. The buttress member may taper in width or thickness as it extends to its distal end, which facilitates insertion of the buttress member during surgery. The buttress member may have an upper surface 2142 (i.e., a bone-engaging surface) for contacting the acromion (see FIGS. 32, 34, and 35). Upper surface 2142 may be rounded along one or more planes, such as rounded along plane 2131$d$ defined by arm 2104 (see FIGS. 32 and 33), and/or rounded along a plane that is orthogonal to plane 2131$d$ (see FIGS. 33 and 34). Upper surface 2142, when rounded, can facilitate sliding travel of buttress member 2106 along the inferior surface of the acromion. This sliding travel enables proper placement of buttress member 2106 against the acromion, and optionally permits dynamic adjustment of the position of buttress member 2106 on the acromion after implantation. A slot 2146 may be formed in the bottom surface (i.e., the outer surface) of buttress member 2106, along a longitudinal axis of buttress member 2106 (see FIG. 33). Slot 2146 may be open at its proximal end and closed (or open) at its distal end, as shown. A pair of coaxial holes 2133 may be defined by a pair of walls 2135 laterally bounding slot 2146 (see FIGS. 32, 34, and 35). Holes 2133 may be located in a longitudinally central region of buttress member 2106, intermediate proximal and distal ends of buttress member 2106. A pin 2138 may extend between spaced holes 2133 of buttress member 2106, via hole 2131$e$ of distal portion 2131$c$, to pivotably connect buttress member 2106 to arm 2104 (see FIGS. 30, 32, and 33). Buttress member 2106 may be pivotally connected to distal portion 2131$c$ at a position spaced from transverse portion 2131$b$ and distal bend 2132$b$. By spacing the site of connection from transverse portion 2131$b$, outrigger 2103 can hold its shape better while remaining engaged more stably with the acromion.

Structures that are "pivotably connected" to one another, as used herein, are able to change their orientations relative to one another, such as by pivoting relative to one another about at least one axis and/or at least one point, while the structures remain connected to one another. The orientations may be adjustable over a continuous range of orientations while the structures remained connected to one another. Exemplary pivotal motion of buttress member 2106 in plane 2131$d$ of arm 2104, and about an axis defined by pin 2138, is indicated at 2137 in FIG. 31 (also see FIG. 33).

One or more radiographic markers 2139 may be present in and/or on buttress member 2106 (see FIGS. 32 and 33). Each radiographic marker 2139 may be radiopaque (e.g., formed of metal) to provide contrast with a body 2141 of buttress member 2106, which may be radiolucent (e.g., formed of polymer). In the depicted embodiment, buttress member 2106 has a pair of radiographic markers 2139 arranged parallel to another and elongated normal to plane 2131$d$. The radiographic markers are attached to body 2141 and embedded therein. With this configuration, each radiographic marker 2139 appears as a dot when radiographically viewed parallel to the radiographic marker (i.e., in an anterior-posterior view of a subject in which device 2100 has been implanted). Arm 2104 (and plate 2102) also may be radiopaque (e.g., formed of metal), which allows the relative orientations of buttress member 2106 and arm 2104 to be viewed radiographically. Accordingly, a surgeon can determine whether the angle of buttress member 2106 has changed during and/or after implantation of device 2100, and/or whether the angle of buttress member 2106 has conformed to the local surface angle of acromion a (as in FIG. 30). In other embodiments, buttress member 2106 may be formed of metal and thus may be radiopaque.

Figure 35:
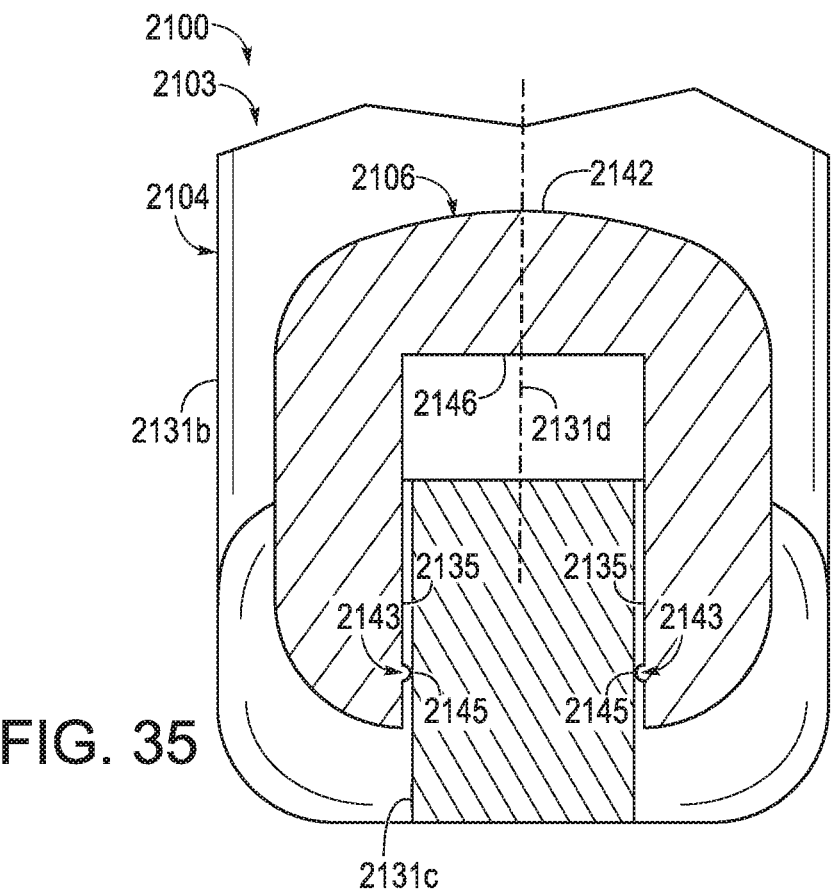
FIG. 35 is a section view of the device of FIG. 27, taken generally along line 35-35 of FIG. 30.

Device 2100 may have at least one friction feature 2143 to increase the friction between arm 2104 and buttress member 2106 (see FIG. 35). Each friction feature independently may be formed by arm 2104 or buttress member 2106. The resistance to turning buttress member 2106 produced by friction feature(s) 2143 collectively may be constant or may vary over the permitted range of orientations of buttress member 2106. The friction can prevent buttress member 2106 from pivoting freely while device 2100 is being implanted, which maintains the shape of outrigger 2103 during insertion and facilitates proper placement of buttress member 2106 under the acromion. Each friction feature 2143 may include a protrusion 2145. In the depicted embodiment, each protrusion 2145 projects from one of walls 2135 into slot 2146. Protrusions 2145 may rub against opposite sides of distal portion 2131c when buttress member 2106 is pivoted. In other examples, one or more protrusions 2145 may be formed on one or both opposite sides of distal portion 2131c, such that each protrusion rubs against one of walls 2135.

Figure 36:
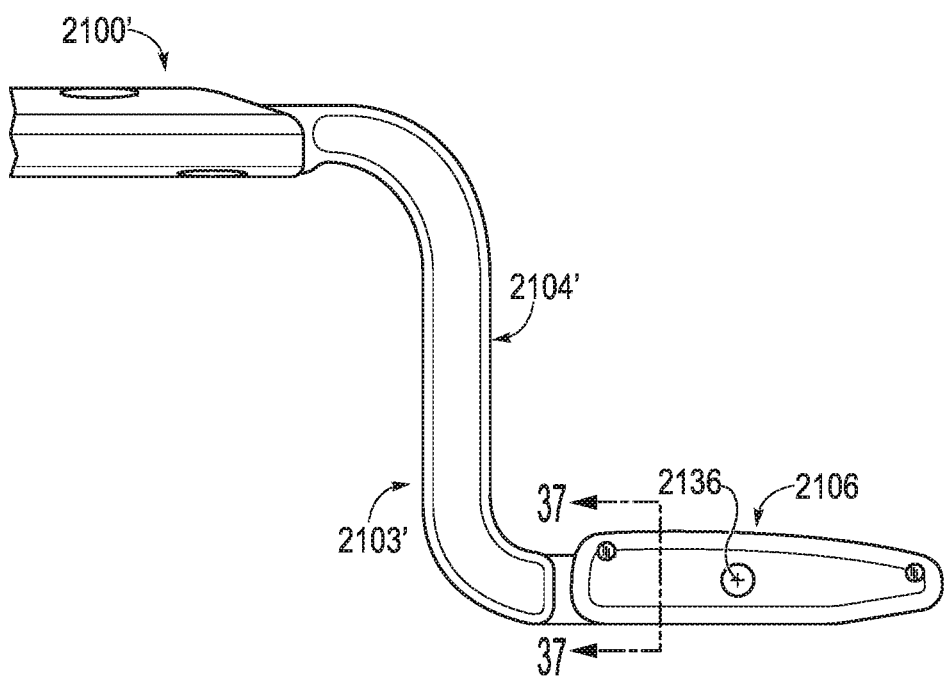
FIG. 36 is a fragmentary side view of a detent-containing device that is similar to the device of FIG. 27, taken generally as in FIGS. 30 and 31, except with the buttress member held parallel to a distal portion of the arm by a pair of detents.
Figure 37:
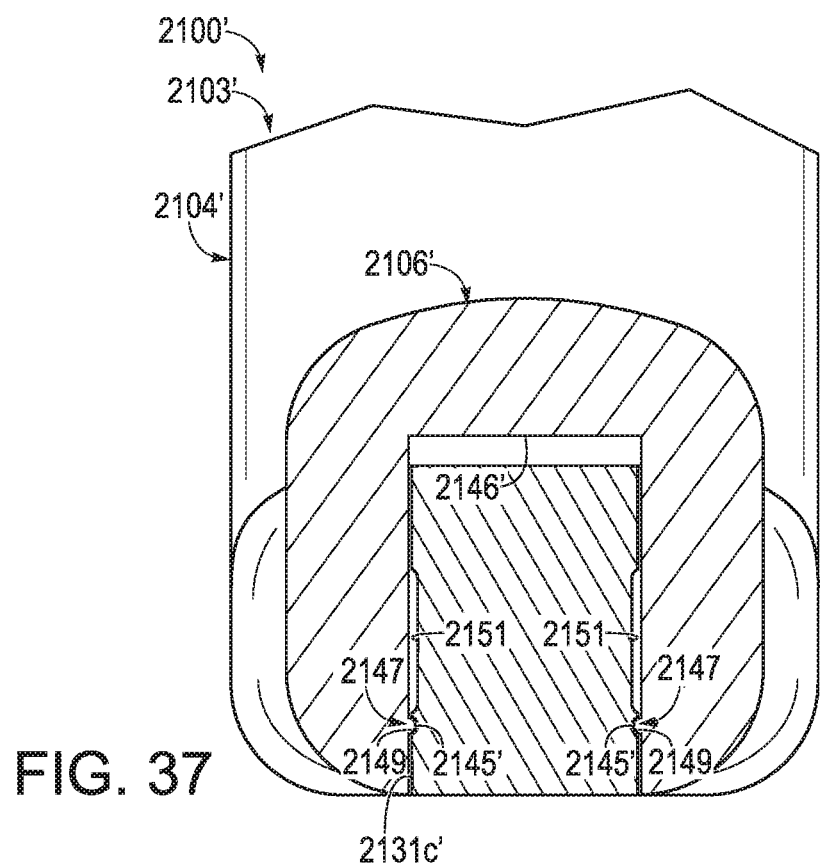
FIG. 37 is a fragmentary section view of the device of FIG. 36, taken generally along line 37-37 of FIG. 36.
Figure 38:
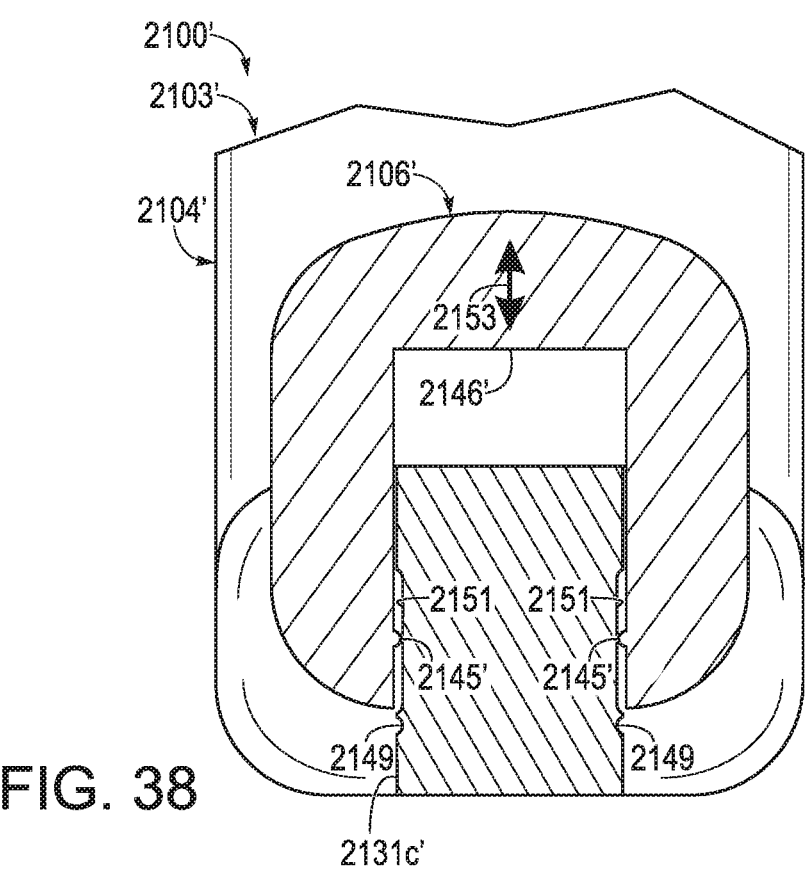
FIG. 38 is another fragmentary section view of the device of FIG. 36, taken generally as in FIG. 37 after disengaging the detents by pivoting the buttress member from the configuration of FIG. 37.

FIGS. 36-38 show portions of a device 2100' having an outrigger 2103'. Device 2100' is identical to device 2100, except that friction features 2143 of device 2100 are replaced with at least one detent, such as a pair of detents 2147 in the depicted embodiment (compare FIGS. 35 and 37). Each detent 2147 utilizes a protrusion 2145', which may be provided by buttress member 2106'. A side wall region of a distal portion 2131c' of arm 2104' may define a corresponding depression 2149 adjacent a slot 2151. Buttress member 2106' has a provisionally fixed configuration when each protrusion 2145' is located in a corresponding depression 2149 (see FIG. 37). Application of at least a threshold torque to buttress member 2106', to urge pivotal motion about a pivot axis 2136 thereof (clockwise in FIG. 36), places buttress member 2106' in a released configuration. More specifically, the torque causes protrusions 2145' to move from depressions 2149 to slots 2151 (compare FIGS. 37 and 38). In the released configuration, buttress member 2106' may be pivotable, indicated by a double-headed arrow at 2153, with application of less than the threshold torque (see FIG. 38). In other embodiments, a protrusion 2145' of at least one detent 2147 may be provided by distal portion 2131c' of arm 2104', and a corresponding depression 2149 and slot 2151 may be defined by buttress member 2106' in slot 2146'.

Figure 39:
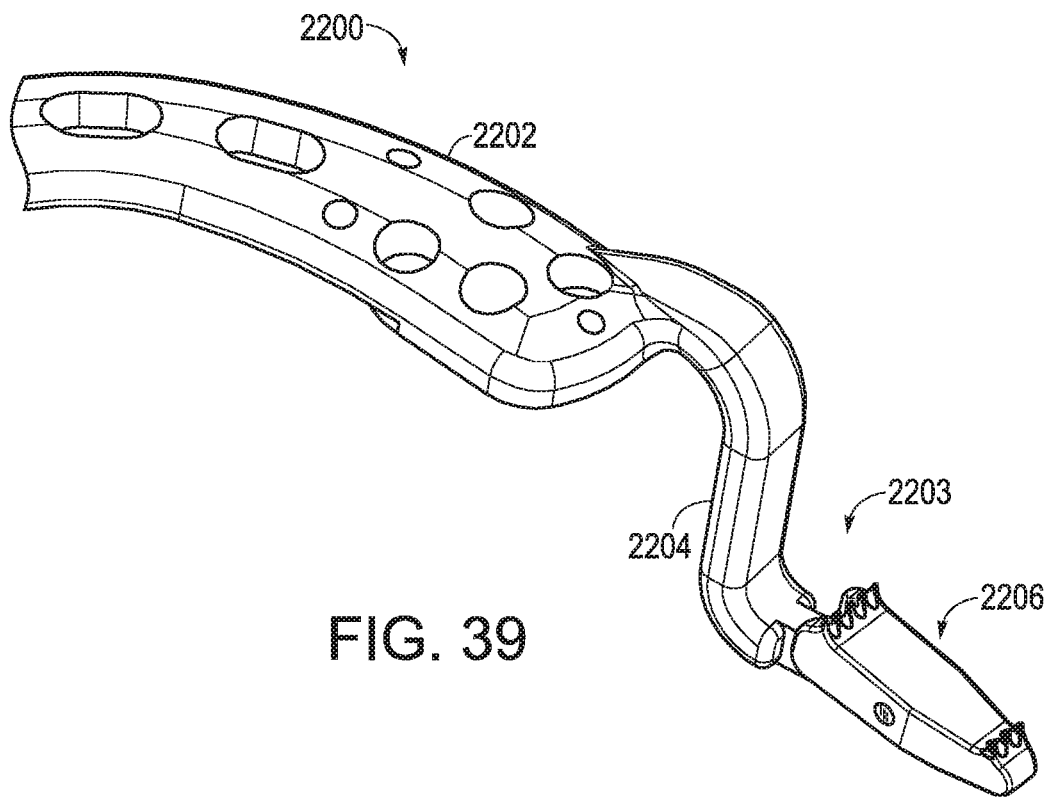
FIG. 39 is a fragmentary view of another exemplary device for stabilizing a clavicle and/or an AC joint, where the device is similar to that of FIG. 27, except the buttress member has protrusions to engage the acromion and resist slippage.
Figure 40:
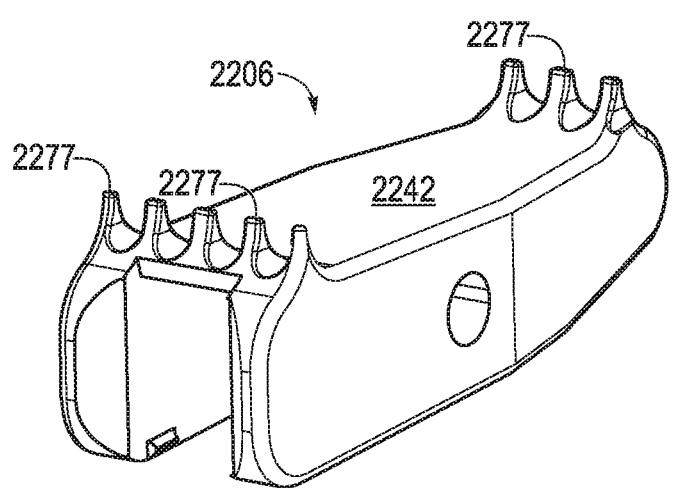
FIG. 40 is a view of the buttress member of the device of FIG. 39, taken in isolation from the main part of the device.

FIGS. 39 and 40 show portions of a device 2200 including a plate 2202 and an outrigger 2203 providing a hook. Device 2200 is identical to device 2100, except that buttress member 2106 of outrigger 2103 has been replaced with a different pivotably-connected buttress member 2206. Buttress member 2206 may be pivotable as described above for buttress member 2106.

An upper surface 2242 (a bone-engaging surface) of buttress member 2206 may be less rounded than bone-engaging surface 2142 of buttress member 2106. One or more protrusions 2277, such as the rows of teeth depicted here, may be defined by upper surface 2242, for engagement with, and optional penetration of, the acromion. Protrusions 2277 may be spikes configured to resist slippage of buttress member 2206 on the acromion after device 2200 has been implanted. Outrigger 2203 may have any suitable combination of features described above for outrigger 2103 of device 2100 (and/or outrigger 2103' of device 2100') (e.g., an arm 2204), such as one or more radiographic markers associated with buttress member 2206, pivotability about only a single pivot axis, one or more friction features, one or more detents, or the like.

Figure 41:
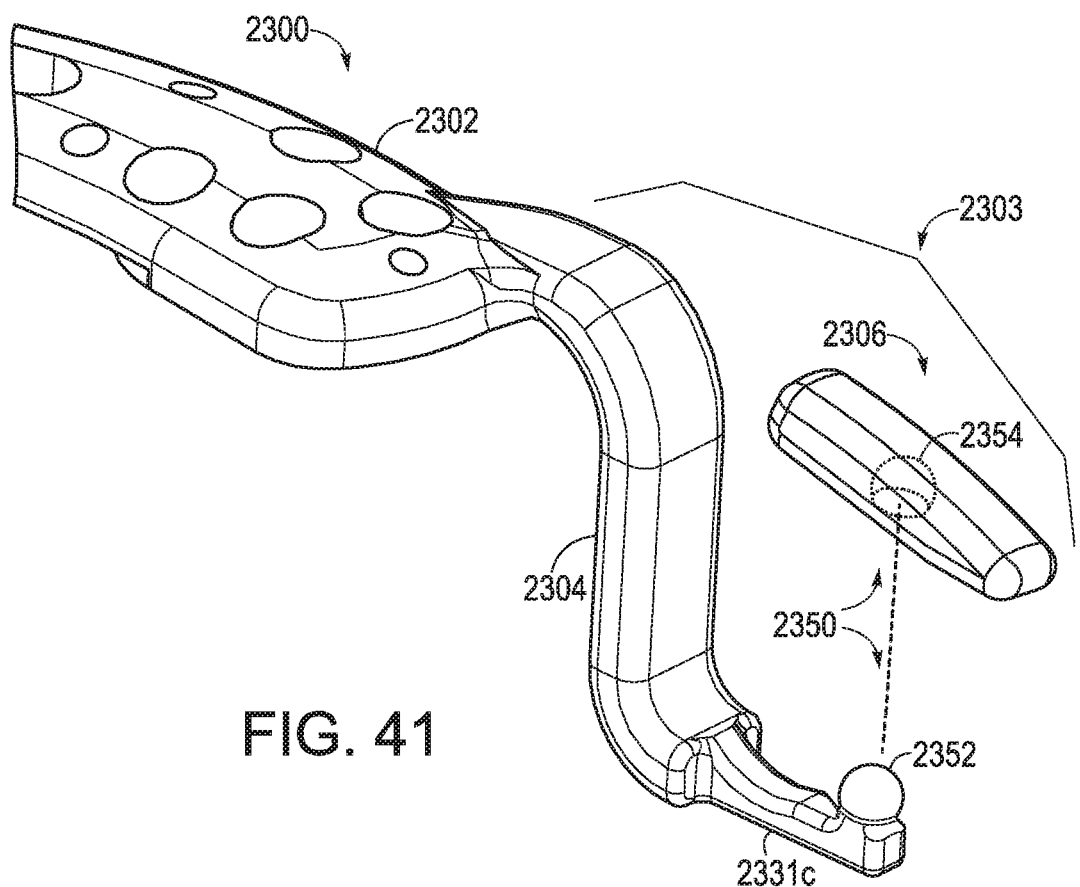
FIG. 41 is a fragmentary view of still another exemplary device for stabilizing a clavicle and/or an AC joint, where the device is similar to that of FIG. 27, except the buttress member is pivotable with respect to the arm in each plane of a plurality of non-parallel planes.
Figure 42:
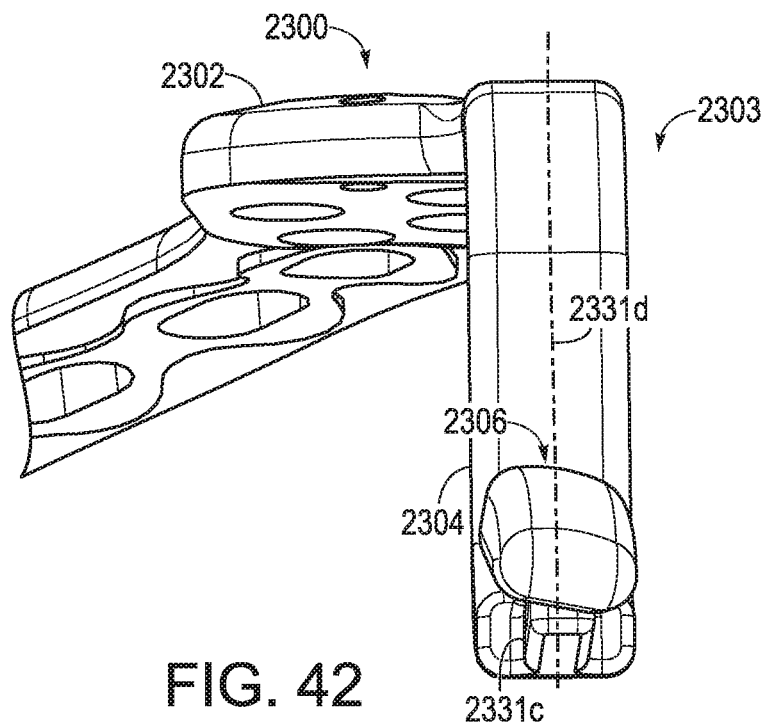
FIG. 42 is an end view of the device of FIG. 41, taken with the buttress member turned from a neutral orientation in a plane that is transverse to a plane defined by the arm.

FIGS. 41 and 42 show portions of a device 2300 for stabilizing bone and including a plate 2302 and an outrigger 2303. The outrigger has an arm 2304 and a buttress member 2306. Device 2300 is identical to device 2100, except that arm 2304 and buttress member 2306 have a different pivotable connection to one another, namely, a ball joint 2350, which provides more degrees of rotational freedom. A distal portion 2331c of arm 2304 has a ball 2352 (i.e., a spherical prominence) at the distal end of arm 2304. A complementary socket 2354 (i.e., a spherical recess) is defined in the underside of buttress member 2306. When fitted together, optionally by a snap fit, buttress member 2306 is retained on ball 2352 and is pivotable with respect to arm 2304 along two or more non-parallel planes, such as along each plane of at least a pair of orthogonal planes or three mutually orthogonal planes. For example, buttress member 2306 may be pivotable in a plane parallel to a plane 2331d defined by buttress member 2306 (similar to plane 2131d of device 2100), to slant buttress member 2306 longitudinally, and also pivotable along a vertical plane that is orthogonal to plane 2331d, to slant buttress member 2306 laterally, as shown in FIG. 42.

iv. Further Aspects

This subsection describes selected aspects of this example as a series of indexed paragraphs.

Paragraph A1. A device for stabilizing a clavicle and/or an acromioclavicular joint, the device comprising: (i) a plate defining a plurality of apertures configured to receive fasteners that secure the plate onto a superior surface region of the clavicle; and (ii) an outrigger providing a hook and including an arm and a buttress member pivotably connected to one another, the arm extending from the plate and having a transverse portion elongated transversely to the plate; wherein the buttress member is configured to be adjustably oriented with respect to the arm by contact between the buttress member and an inferior surface region of an acromion of the acromioclavicular joint.

Paragraph A2. The device of paragraph A1, wherein the buttress member is pivotable with respect to the arm while remaining connected to the arm.

Paragraph A3. The device of paragraph A2, wherein the buttress member is pivotable with respect to the arm about at least one axis and/or about a point.

Paragraph A4. The device of paragraph A3, wherein the arm has a distal portion, wherein each of the transverse portion and the distal portion of the arm is elongated along a plane, and wherein the buttress member is pivotable with respect to the arm about an axis that is transverse to the plane.

Paragraph A5. The device of any of paragraphs A1 to A4, wherein the buttress member is adjustably orientable with respect to the arm over a continuous range of orientations while remaining connected to the arm.

Paragraph A6. The device of any of paragraphs A1 to A5, wherein the plate is elongated between a pair of end regions, and wherein the arm extends from one of the end regions.

Paragraph A7. The device of any of paragraphs A1 to A6, wherein the plate and the arm are formed integrally with one another.

Paragraph A8. The device of any of paragraphs A1 to A7, wherein the arm has a distal end that is spaced from the plate, and wherein the buttress member extends distally beyond the distal end.

Paragraph A9. The device of paragraph A8, wherein the arm comprises a distal portion including the distal end, wherein the arm forms a bend between the transverse portion and the distal portion, and wherein the buttress member is pivotably connected to the distal portion at a position that is closer to the distal end than the bend.

Paragraph A10. The device of any of paragraphs A1 to A9, wherein the buttress member is elongated between opposite ends of the buttress member, and wherein the buttress member is pivotably connected to the arm at a central region of the buttress member intermediate the opposite ends.

Paragraph A11. The device of any of paragraphs A1 to A10, wherein the outrigger includes at least one friction feature or detent that prevents the buttress member from turning relative to the arm until at least a threshold torque is applied to the buttress member.

Paragraph A12. The device of paragraph A11, wherein the buttress member is configured to be released in response to application of the at least a threshold torque, such that turning the released buttress member requires application of less than the threshold torque.

Paragraph A13. The device of any of paragraphs A1 to A12, wherein the buttress member includes at least one radiopaque marker attached to a radiolucent body.

Paragraph A14. The device of any of paragraphs A1 to A13, further comprising any limitation or combination of limitations of paragraphs B1, B2, and C1 to C21 of this section.

Paragraph B1. A device for stabilizing a clavicle and/or an acromioclavicular joint, the device comprising: (i) a plate defining a plurality of apertures configured to receive fasteners that secure the plate onto a superior surface region of the clavicle; and (ii) an outrigger providing a hook and including an arm and a buttress member, the arm extending from the plate and having a transverse portion elongated transversely to the plate and located along the arm intermediate the plate and the buttress member; wherein the buttress member is pivotably connected to the arm and configured to be placed against an inferior surface region of an acromion of the acromioclavicular joint, and wherein, optionally, the arm is formed integrally with the plate.

Paragraph B2. The device of paragraph B1, wherein the buttress member is adjustable with respect to the arm over a continuous range of orientations while remaining connected to the arm.

Paragraph B3. The device of paragraph B1 or B2, further comprising any limitation or combination of limitations of paragraphs A1 to A13 and C1 to C21 of this section.

Paragraph C1. A device for stabilizing a clavicle and/or an acromioclavicular joint, the device comprising: (i) a plate defining a plurality of apertures configured to receive fasteners that secure the plate onto a superior surface region of the clavicle; and (ii) an outrigger providing a hook and including an arm and a buttress member, the arm having a first end and a second end, the arm extending from the plate via the first end and including a transverse portion and a distal portion, the distal portion including the second end, the transverse portion being transverse to the plate and the distal portion; wherein the buttress member is configured to be placed against an inferior surface region of an acromion of the acromioclavicular joint, and wherein the buttress member is pivotably connected to the arm at the distal portion, at a position spaced from the transverse portion of the arm.

Paragraph C2. The device of paragraph C1, wherein the arm forms a bend between the transverse portion and the distal portion, and wherein the buttress member is pivotably connected to the distal portion at a position that is closer to the second end than the bend.

Paragraph C3. The device of paragraph C2, wherein the buttress member is pivotably connected to the distal portion at the second end of the arm.

Paragraph C4. The device of any of paragraphs C1 to C3, wherein the buttress member extends distally beyond the second end of the arm.

Paragraph C5. The device of paragraph C4, wherein the buttress member is elongated between opposite ends of the buttress member, and wherein the buttress member is pivotably connected to the distal portion at a central region of the buttress member intermediate the opposite ends.

Paragraph C6. The device of any of paragraphs C1 to C5, wherein the arm and the plate are formed integrally with one another.

Paragraph C7. The device of any of paragraphs C1 to C6, wherein the buttress member is pivotable with respect to the arm about an axis.

Paragraph C8. The device of paragraph C7, further comprising a pin that pivotably connects the buttress member to the arm for rotation about an axis defined by the pin.

Paragraph C9. The device of any of paragraphs C1 to C8, wherein the buttress member is pivotable with respect to the arm in at least one plane.

Paragraph C10. The device of any of paragraphs C1 to C9, wherein the buttress member is pivotable with respect to the arm in each plane of two or more non-parallel planes.

Paragraph C11. The device of paragraph C10, wherein the buttress member is pivotable with respect to the arm in each plane of three mutually orthogonal planes.

Paragraph C12. The device of any of paragraphs C1 to C11, wherein the outrigger includes at least one friction feature or detent that prevents the buttress member from turning relative to the arm until at least a threshold torque is applied to the buttress member.

Paragraph C13. The device of paragraph C12, wherein the outrigger includes at least one detent, and wherein the buttress member is configured to be released in response to application of the at least a threshold torque, such that turning the released buttress member requires less than the threshold torque.

Paragraph C14. The device of any of paragraphs C1 to C13, wherein the buttress member includes at least one radiopaque marker attached to a radiolucent body.

Paragraph C15. The device of paragraph C14, wherein the at least one radiopaque marker is configured to be visible in an anterior-posterior fluoroscopic view of the device implanted in a subject.

Paragraph C16. The device of paragraph C14 or C15, wherein a position of the at least one radiopaque marker relative to the arm is configured to indicate whether the buttress member has turned with respect to the arm in the subject.

Paragraph C17. The device of any of paragraphs C1 to C16, wherein the buttress member defines one or more protrusions configured to engage the acromion to resist slippage of the buttress member on the inferior surface region of the acromion.

Paragraph C18. The device of any of paragraphs C1 to C17, wherein the buttress member has a rounded acromion-contacting surface region configured to permit the buttress member to slide on the inferior surface region of the acromion.

Paragraph C19. The device of any of paragraphs C1 to C18, wherein the arm includes a proximal portion located along the arm between the plate and the transverse portion of the arm.

Paragraph C20. The device of paragraph C19, wherein the arm forms an angle of 60-120 degrees at a junction between the proximal portion and the transverse portion.

Paragraph C21. The device of any of paragraphs C1 to C20, wherein the arm forms an angle of 60-120 degrees between the transverse portion and the distal portion.

Paragraph C22. The device of any of paragraphs C1 to C21, further comprising any limitation or combination of limitations of paragraphs A1 to A13, B1, and B2 of this section.

Paragraph D1. A method of stabilizing a clavicle and/or an acromioclavicular joint, the method comprising: (i) selecting the device of any of paragraphs A-C of Section II; (ii) placing the plate of the device onto the superior surface region of the clavicle, and the buttress member of the device in contact with the inferior surface region of the acromion; and (iii) securing the plate onto the superior surface region of the clavicle with fasteners.

Paragraph E1. A method of stabilizing a clavicle and/or an acromioclavicular joint using a device including a plate and a hook, the hook including an arm and a buttress member pivotably connected to one another, the method comprising: (i) adjusting an orientation of the buttress member with respect to the arm by placing the buttress member against an inferior surface region of an acromion of the acromioclavicular joint; and (ii) securing the plate onto a superior surface region of the clavicle.

Paragraph E2. The method of paragraph E1, further comprising any limitation or combination of limitations of paragraphs A1 to A13, B1, B2, and C1 to C21 of this section.

Example 21. Selected Aspects

This example describes selected aspects of the present disclosure as a series of indexed paragraphs.

Paragraph F1. A device for stabilizing bone, the device comprising: (i) a plate defining one or more apertures configured to receive one or more fasteners that secure the plate onto a first bone region; (ii) an arm projecting from an edge of the plate; and (iii) a buttress member connected pivotably to an end of the arm; wherein the buttress member is configured to be pivoted by contact with a second bone region to conform the orientation of the buttress member to the second bone region, and wherein, optionally, the buttress member is configured to apply compression to, and/or support, the second bone region using force transmitted to the buttress member via the arm.

Paragraph F2. The device of paragraph F1, wherein the buttress member is configured to apply compression to the second bone region without being secured to the second bone region using a fastener(s) that extends into an aperture(s) defined by the buttress member.

Paragraph F3. The device of paragraph F1 or F2, wherein the buttress member does not define any apertures configured to receive fasteners for securing the buttress member to the second bone region.

Paragraph F4. The device of any of paragraphs F1 to F3, wherein the arm is formed integrally with the plate.

Paragraph F5. The device of any of paragraphs F1 to F4, wherein the arm extends longitudinally or laterally from the plate.

Paragraph F6. The device of any of paragraphs F1 to F3 and F5, wherein the arm and the plate are formed separately from one another.

Paragraph F7. The device of paragraph F6, wherein the arm and the plate are movably connected to one another.

Paragraph F8. The device of paragraph F7, wherein the arm is adjustably extendable from the plate to change a distance between the plate and the end of the arm to which the buttress member is connected pivotably, and wherein the arm is configured to be lockable to the plate to fix the distance between the plate and the end of the arm.

Paragraph F9. The device of any of paragraphs F1 to F8, wherein the buttress member is pivotable with respect to the arm about a single pivot axis.

Paragraph F10. The device of paragraph F9, wherein the single pivot axis is orthogonal to a plane, wherein the buttress member has an inner surface to contact the second bone region, and wherein the plane is transverse to the inner surface of the buttress member.

Paragraph F11. The device of paragraph F10, wherein the plane is substantially orthogonal to the inner surface of the buttress member.

Paragraph F12. The device of any of paragraphs F9 to F11, wherein the buttress member is pivotable about a single axis that is transverse to the plate.

Paragraph F13. The device of any of paragraphs F1 to F8, wherein the buttress member is pivotable with respect to the arm in each plane of two or more non-parallel planes, and wherein the buttress member is connected pivotably to the arm at a centroid region of the buttress member.

Paragraph F14. The device of any of paragraphs F1 to F13, wherein the device includes a plurality of outriggers, and wherein each outrigger includes an arm projecting from an edge of the plate and a buttress member pivotably connected to the arm.

Paragraph F15. The device of any of paragraphs F1 to F14, wherein the arm has a first end opposite a second end, wherein the arm is pivotably connected to the plate at the first end, and wherein the arm is pivotably connected to the buttress member at the second end.

Paragraph F16. The device of any of paragraphs F1 to F15, wherein the arm is elongated along a plane, and wherein the buttress member is pivotable with respect to the arm about an axis that is transverse to the plane.

Paragraph F17. The device of any of paragraphs F1 to F16, wherein the plate is elongated between a pair of end regions, and wherein the arm projects from one of the end regions or from a lateral edge region of the plate located intermediate the end regions.

Paragraph F18. The device of any of paragraphs F1 to F17, wherein the arm has a distal end that is spaced from the plate, and wherein the buttress member extends distally beyond the distal end.

Paragraph F19. The device of paragraph F18, wherein the arm includes a transverse portion and distal portion, wherein the distal portion includes the distal end, wherein the arm forms a bend between the transverse portion and the distal portion, and wherein the buttress member is connected to the distal portion at a position that is closer to the distal end than the bend.

Paragraph F20. The device of any of paragraphs F1 to F19, wherein the buttress member is elongated along opposite lateral edges between opposite ends, and wherein the buttress member is connected to the arm at a central region of the buttress member intermediate the lateral edges and/or the opposite ends.

Paragraph F21. The device of any of paragraphs F1 to F20, wherein the device includes at least one friction feature or detent that prevents the buttress member from pivoting relative to the arm until at least a threshold torque is applied to the buttress member, and wherein the buttress member is configured to be released in response to application of the at least a threshold torque, such that pivoting the buttress member after the buttress member has been released requires application of less than the threshold torque.

Paragraph F22. The device of any of paragraphs F1 to F21, wherein the buttress member includes at least one radiopaque marker attached to a radiolucent body.

Paragraph F23. The device of any of paragraphs F1 to F22, wherein the buttress member is configured to be freely pivotable with respect to the arm over a continuous range of orientations while remaining connected to the arm.

Paragraph F24. The device of any of paragraphs F1 to F23, wherein the buttress member includes an inner surface to contact the second bone region, and wherein the inner surface defines one or more spikes.

Paragraph F25. The device of any of paragraphs F1 to F24, wherein the first bone region and the second bone region are provided by different bones of a subject.

Paragraph F26. The device of paragraph F25, wherein the first bone region is a superior surface region of a clavicle, and wherein the second bone region is an inferior surface region of an acromion.

Paragraph F27. The device of any of paragraphs F1 to F24, wherein the first bone region and the second bone region are provided by the same bone of a subject.

Paragraph F28. The device of paragraph F27, wherein the first bone region and the second bone region are arranged along a proximal femur.

Paragraph F29. The device of any of paragraphs F1 to F28, wherein the first bone region and the second bone region are provided by a pelvis.

Paragraph F30. The device of any of paragraphs F1 to F29, wherein the second bone region is associated with an anatomical joint.

Paragraph F31. The device of paragraph F30, wherein the buttress member is configured to expand an articular region of the anatomical joint and/or discourage dislocation at the anatomical joint.

Paragraph F32. The device of paragraph F31, wherein the buttress member is configured to contact bone at or near the glenoid rim, and to discourage dislocation or subluxation of a humeral head from the glenoid.

Paragraph F33. A method of stabilizing bone, the method comprising: selecting the device of any of paragraphs F1 to F32; placing the plate onto the first bone region, and the buttress member in contact with the second bone region; and securing the plate onto the first bone region with one or more fasteners.

Paragraph G1. A method of stabilizing bone, the method comprising: (i) selecting a device including (1) a plate configured to be placed onto a first bone region, (2) an arm projecting from an edge of the plate, and (3) a buttress member connected pivotably to an end of the arm; (ii) placing the plate against a first bone region, and the buttress member against a second bone region to conform the orientation of the buttress member to the second bone region, such that compression is applied to the second bone region using force transmitted from the plate to the buttress member via the arm; and (iii) securing the plate to the first bone region.

Paragraph G2. The method of paragraph G1, wherein the first bone region and the second bone region are provided by the same fractured bone, and wherein placing includes reducing the fractured bone using the device.

Paragraph G3. The method of paragraph G1 or G2, wherein the buttress member applies compression to the second bone region without being secured to the second bone region using a fastener formed separately from the buttress member.

Paragraph G4. The method of any of paragraphs G1 to G3, wherein the plate defines one or more apertures, and wherein securing includes securing the plate to the first bone region using one or more fasteners at the one or more apertures.

Paragraph G5. The method of any of paragraphs G1 to G4, wherein the arm is formed integrally with the plate.

Paragraph G6. The method of any of paragraphs G1 to G5, wherein the arm extends longitudinally or laterally from the plate.

Paragraph G7. The method of any of paragraphs G1 to G6, wherein the arm and the plate are formed separately from one another and are connected movably and lockably to one another.

Paragraph G8. The method of paragraph G7, further comprising adjusting a length of the arm that projects from the edge of the plate, and locking the arm to the plate to fix the length.

Paragraph G9. The method of any of paragraphs G1 to G8, wherein the buttress member is pivotable with respect to the arm about a single pivot axis.

Paragraph G10. The method of paragraph G9, wherein the buttress member has a bone-engaging surface, and wherein the single pivot axis is generally and/or substantially parallel to the bone-engaging surface.

Paragraph G11. The method of any of paragraphs G1 to G8, wherein the buttress member is pivotable with respect to the arm about each axis of two or more non-parallel axes, and wherein the buttress member is connected pivotably to the arm at or near a centroid region of the buttress member.

Paragraph G12. The method of any of paragraphs G1 to G11, wherein the buttress member is not secured to the second bone region using a fastener that extends into an aperture defined by the buttress member.

Paragraph G13. The method of any of paragraphs G1 to G12, wherein the device includes a plurality of outriggers, wherein each outrigger includes an arm projecting from an edge of the plate and a buttress member pivotably connected to the arm, and wherein placing includes placing two or more of the plurality of buttress members against the second bone region.

Paragraph G14. The method of any of paragraphs G1 to G13, wherein the first bone region and the second bone region are provided by the same bone.

Paragraph G15. The method of paragraph G14, wherein the first bone region and the second bone region are arranged along a proximal femur.

Paragraph G16. The method of any of paragraphs G1 to G15, wherein the second bone region is associated with an anatomical joint.

Paragraph G17. The method of any of paragraphs G1 to G16, wherein the buttress member is configured to expand an articular region of the anatomical joint and/or discourage dislocation or subluxation at the anatomical joint.

Paragraph G18. The method of paragraph G17, wherein the buttress member contacts bone at or near the glenoid rim and discourages dislocation or subluxation of a humeral head from the glenoid.

Paragraph G19. The method of any of paragraphs G1 to G13 and G16 to G18 wherein the first bone region and the second bone region are provided by different bones.

Paragraph G20. The method of paragraph G19, wherein the first bone region is a superior surface region of a clavicle, and wherein the second bone region is an inferior surface region of an acromion.

Paragraph G21. The method of any of paragraphs G1 to G12 and G14 to G17, wherein the first bone region is provided by a rib, and wherein the second bone region is provided by sternum.

Paragraph G22. The method of paragraph G21, wherein the device is implanted in a subject undergoing surgery for pectus excavatum.

Paragraph G23. The method of any of any of paragraphs G1 to G22, wherein the first bone region and the second bone region are provided by a pelvis.

Paragraph G24. The method of any of paragraphs G1 to G23, performed with the device of any of paragraphs F1 to F32.

The term "exemplary" as used in the present disclosure, means "illustrative" or "serving as an example." Similarly, the term "exemplify" means "to illustrate by giving an example." Neither term implies desirability or superiority.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

We claim:

1. A device for stabilizing bone, the device comprising:
   a plate defining one or more apertures configured to receive one or more fasteners that secure the plate onto a first bone region;
   an arm projecting from an edge of the plate; and
   a buttress member connected pivotably to an end of the arm,
   wherein the buttress member is configured to be pivoted by contact with a second bone region to conform an orientation of the buttress member to the second bone region, and to apply compression to, and/or support, the second bone region using force transmitted to the buttress member via the arm and without being secured to the second bone region.

2. The device of claim 1, wherein the buttress member is configured to apply compression to the second bone region without being secured to the second bone region using a fastener(s) that extends into an aperture(s) defined by the buttress member.

3. The device of claim 1, wherein the buttress member does not define any apertures configured to receive fasteners for securing the buttress member to the second bone region.

4. The device of claim 1, wherein the arm is formed integrally with the plate.

5. The device of claim 1, wherein the buttress member is pivotable with respect to the arm about a single pivot axis.

6. The device of claim 5, wherein the single pivot axis is orthogonal to a plane, wherein the buttress member has an inner surface to contact the second bone region, and wherein the plane is transverse to the inner surface of the buttress member.

7. The device of claim 6, wherein the plane is substantially orthogonal to the inner surface of the buttress member.

8. The device of claim 1, wherein the buttress member is pivotable with respect to the arm about each of two or more non-parallel axes, and wherein the buttress member is connected pivotably to the arm at or near a centroid region of the buttress member.

9. The device of claim 1, wherein the device comprises a plurality of arms and a plurality of buttress members each pivotably connected to a respective arm of the plurality of arms.

10. The device of claim 1, wherein the buttress member is configured to contact bone at or near a glenoid rim of a glenoid, and to discourage dislocation or subluxation of a humeral head from a glenohumeral joint.

11. A device for stabilizing bone, the device comprising:
    a plate defining one or more apertures configured to receive one or more fasteners that secure the plate onto a first bone region;
    an arm projecting from an edge of the plate; and
    a buttress member connected pivotably to an end of the arm, wherein the buttress member is pivotable with respect to the arm about a single pivot axis,
    wherein the buttress member is configured to be pivoted by contact with a second bone region to conform an orientation of the buttress member to the second bone region,
    wherein the arm is adjustably extendable from the plate to change a distance between the plate and the end of the arm to which the buttress member is connected pivotably, and wherein the arm is configured to be lockable to the plate to fix the distance between the plate and the end of the arm,
    wherein the buttress member is configured to apply compression to, and/or support, the second bone region without being secured to the second bone region.

12. The device of claim 11, wherein the arm is interchangeably lockable to the plate at only a discrete series of positions.

13. The device of claim 11, wherein the buttress member is configured to apply compression to the second bone region without being secured to the second bone region using a fastener(s) that extends into an aperture(s) defined by the buttress member.

14. The device of claim 11, wherein the single pivot axis is orthogonal to a plane, wherein the buttress member has an inner surface to contact the second bone region, and wherein the plane is transverse to the inner surface of the buttress member.

15. A device for stabilizing bone, the device comprising:
a plate defining one or more apertures configured to receive one or more fasteners that secure the plate onto a first bone region;
a plurality of outriggers, each outrigger including an arm projecting from an edge of the plate and a buttress member pivotably connected to the arm,
wherein each buttress member is configured to be pivoted by contact with a second bone region to conform an orientation of the buttress member to the second bone region,
wherein each buttress member is configured to apply compression to, and/or support, the second bone region without being secured to the second bone region.

16. The device of claim 15, wherein each arm is formed integrally with the plate.

17. The device of claim 15, wherein the plate has a pair of lateral edges, and wherein each arm projects from the same lateral edge of the pair of lateral edges.

18. A device for stabilizing bone, the device comprising:
a plate defining one or more apertures configured to receive one or more fasteners that secure the plate onto a first bone region;
an arm projecting from an edge of the plate; and
a buttress member connected pivotably to an end of the arm,
wherein the buttress member is configured to be pivoted by contact with a second bone region to conform an orientation of the buttress member to the second bone region, wherein the arm has a first end opposite a second end, wherein the arm is pivotably connected to the plate at the first end about a fixed pivot axis, and wherein the arm is pivotably connected to the buttress member at the second end,
wherein the buttress member is configured to apply compression to, and/or support, the second bone region without being secured to the second bone region.

19. The device of claim 18, wherein the arm is lockable to the plate to fix an orientation of the arm and the plate relative to one another.

20. A device for stabilizing bone, the device comprising:
a plate defining one or more apertures configured to receive one or more fasteners that secure the plate onto a first bone region;
an arm projecting from an edge of the plate; and
a buttress member connected pivotably to an end of the arm,
wherein the buttress member is configured to be pivoted by contact with a second bone region associated with an anatomical joint to conform an orientation of the buttress member to the second bone region, wherein the buttress member is configured to expand an articular region of the anatomical joint and/or discourage dislocation or subluxation at the anatomical joint, and wherein a surface of the buttress member that contacts the second bone region is configured for articulation such that the second bone region may articulate relative to the surface of the buttress member.

21. The device of claim 20, wherein the buttress member is configured to contact bone at or near a glenoid rim of a glenoid, and to discourage dislocation or subluxation of a humeral head from a glenohumeral joint.

* * * * *